(12) United States Patent
Evgey

(10) Patent No.: US 12,705,299 B2
(45) Date of Patent: Aug. 11, 2026

(54) SYSTEM FOR EMPOWERING PDF FILES WITH ENTERPRISE MESSAGING CONNECTIVITY, FORMS, AND LIVE VIDEO WITHOUT CODING

(71) Applicant: David Evgey, Baltimore, MD (US)

(72) Inventor: David Evgey, Baltimore, MD (US)

( * ) Notice: Subject to any disclaimer, the term of this patent is extended or adjusted under 35 U.S.C. 154(b) by 0 days.

(21) Appl. No.: 19/530,447

(22) Filed: Feb. 5, 2026

(65) Prior Publication Data

US 2026/0170077 A1 Jun. 18, 2026

Related U.S. Application Data

(63) Continuation-in-part of application No. 17/084,850, filed on Oct. 30, 2020, now Pat. No. 12,598,150.

(51) Int. Cl.
*G06F 16/958* (2019.01)
*G06F 40/166* (2020.01)
*G16H 80/00* (2018.01)

(52) U.S. Cl.
CPC .......... *G06F 16/958* (2019.01); *G06F 40/166* (2020.01); *G16H 80/00* (2018.01)

(58) Field of Classification Search
None
See application file for complete search history.

(56) References Cited

U.S. PATENT DOCUMENTS

2011/0270923 A1* 11/2011 Jones ...................... G06F 3/044 709/204
2012/0017153 A1* 1/2012 Matsuda ............. G11B 27/034 715/725
2013/0240618 A1* 9/2013 Hall .................... G06F 16/9554 235/375
2014/0108959 A1* 4/2014 Choupak ............... H04L 65/403 715/753
2014/0111597 A1* 4/2014 Anderson ............. H04N 7/157 348/14.03
2018/0027210 A1* 1/2018 Du .......................... H04L 51/48 348/14.01

* cited by examiner

*Primary Examiner* — Maikhanh Nguyen

(57) ABSTRACT

The present invention relates to a system for providing live, interactive portable document format (PDF) documents that function as real-time, network-connected execution environments. The system transforms conventional static PDFs into interactive documents capable of supporting real-time communication, structured data exchange, multimedia interaction, and collaborative workflows without requiring browser plugins, extensions, or standalone software installations. The system comprises a document generation and execution module for creation of interactive PDFs from scratch or enhancement of existing PDFs using configurable options for text, images, video, audio, forms, reports, and links. The interactive PDFs is embedded with multiple interfaces for real-time chat, audio and video communication, payment processing, scheduling, database lookup, media playback, and dynamic chart generation. Upon execution, the interactive PDF enables secure, bi-directional collaboration, data management, and multimedia interaction directly within the document interface.

17 Claims, 21 Drawing Sheets

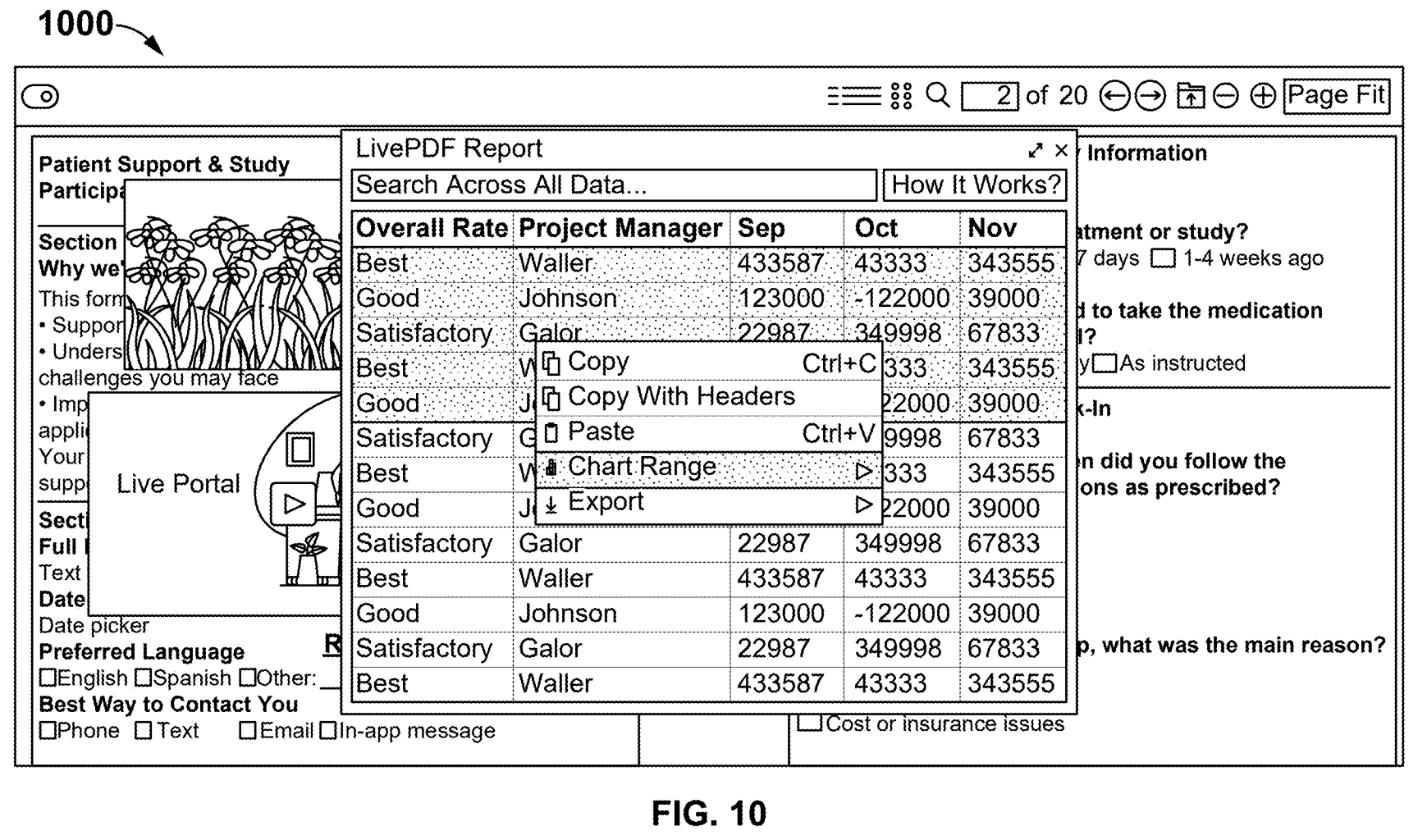

1000

| Overall Rate | Project Manager | Sep | Oct | Nov |
|---|---|---|---|---|
| Best | Waller | 433587 | 43333 | 343555 |
| Good | Johnson | 123000 | -122000 | 39000 |
| Satisfactory | Galor | 22987 | 349998 | 67833 |
| Best | W |  | 333 | 343555 |
| Good | J |  | 22000 | 39000 |
| Satisfactory | G |  | 9998 | 67833 |
| Best | W |  | 333 | 343555 |
| Good | J |  | 22000 | 39000 |
| Satisfactory | Galor | 22987 | 349998 | 67833 |
| Best | Waller | 433587 | 43333 | 343555 |
| Good | Johnson | 123000 | -122000 | 39000 |
| Satisfactory | Galor | 22987 | 349998 | 67833 |
| Best | Waller | 433587 | 43333 | 343555 |

FIG. 10

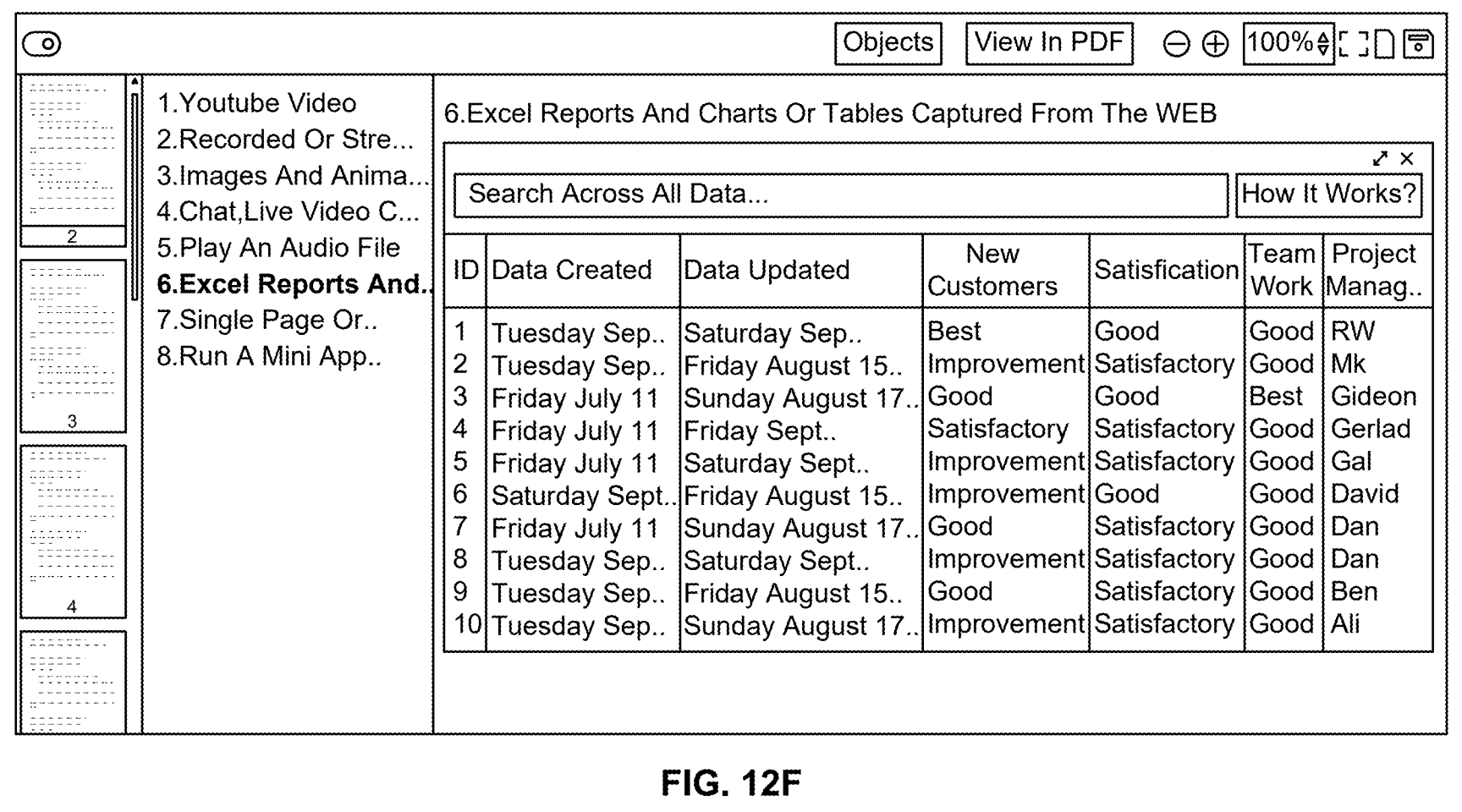

Objects | View In PDF | 100%

2
3
4

1.Youtube Video
2.Recorded Or Stre...
3.Images And Anima...
4.Chat,Live Video C...
5.Play An Audio File
6.Excel Reports And..
7.Single Page Or..
8.Run A Mini App..

6.Excel Reports And Charts Or Tables Captured From The WEB

Search Across All Data... | How It Works?

| ID | Data Created | Data Updated | New Customers | Satisfication | Team Work | Project Manag.. |
|---|---|---|---|---|---|---|
| 1 | Tuesday Sep.. | Saturday Sep.. | Best | Good | Good | RW |
| 2 | Tuesday Sep.. | Friday August 15.. | Improvement | Satisfactory | Good | Mk |
| 3 | Friday July 11 | Sunday August 17.. | Good | Good | Best | Gideon |
| 4 | Friday July 11 | Friday Sept.. | Satisfactory | Satisfactory | Good | Gerlad |
| 5 | Friday July 11 | Saturday Sept.. | Improvement | Satisfactory | Good | Gal |
| 6 | Saturday Sept.. | Friday August 15.. | Improvement | Good | Good | David |
| 7 | Friday July 11 | Sunday August 17.. | Good | Satisfactory | Good | Dan |
| 8 | Tuesday Sep.. | Saturday Sept.. | Improvement | Satisfactory | Good | Dan |
| 9 | Tuesday Sep.. | Friday August 15.. | Good | Satisfactory | Good | Ben |
| 10 | Tuesday Sep.. | Sunday August 17.. | Improvement | Satisfactory | Good | Ali |

FIG. 12F

SYSTEM FOR EMPOWERING PDF FILES WITH ENTERPRISE MESSAGING CONNECTIVITY, FORMS, AND LIVE VIDEO WITHOUT CODING

CROSS REFERENCE TO RELATED APPLICATION

The present application is a continuation-in-part of the U.S. patent application Ser. No. 17/084,850, filed on Oct. 30, 2020 (now U.S. Pat. No. 12,598,150), the contents of which is hereby incorporated by reference.

BACKGROUND OF THE INVENTION

A. Technical Field

The present invention specifically relates to portable document format (PDF) documents and, more particularly, to a system and method for enabling post-creation insertion and execution of interactive-text or image-links and content within existing PDF documents or creating a PDF document and inserting these interactive links, using the same core technology and network-connected, link-activated execution disclosed in U.S. patent application Ser. No. 17/084,850. Specifically, the present invention involves detecting links, and determining whether such links are associated with LiveNetworks™ and if positive what type of service is requested. Both, the domain name as well as the type of service requested can be extracted from the detected links. Upon detecting a link that is associated with a LiveNetworks™, the system is configured to execute one or more services on top of an interactive PDF document or application. Further, the present invention relates to an interactive PDF system in which a PDF, whether newly generated or previously created, executes as a real-time, browser-accessible, network-connected interactive environment that supports in-document execution of communication interfaces, multimedia content, reports, charts, and data exchange, all activated right inside or on top of the PDF document, without requiring proprietary PDF authoring software, browser plugins, extensions, or a user to exit the document.

B. Description of Related Art

Portable document format (PDF) is the world's most widely used document format for distribution of digital content due to its consistent rendering and portability across devices and software environments. PDFs are widely used for e-books, official records, forms, reports, legal documents, and other printable or archival materials. Conventional PDFs, however, are primarily designed, with the exception of links that will cause the browser to leave the application, temporarily or permanently, and load other web pages, as static documents. While certain PDFs may permit limited editing of text or images through proprietary authoring tools, the fundamental structure of a PDF is not designed to function as a network-connected execution environment.

A significant limitation of conventional PDFs arises after a PDF has been generated. Once created, inserting, modifying, or retrofitting executable links, interactive services, or dynamic content into an existing PDF is difficult, unreliable, or impossible without access to proprietary PDF authoring software. In many cases, the internal structure or encryption of a PDF prevents meaningful post-creation insertion of links or interactive elements, particularly by users who do not possess specialized editing tools. As a result, existing PDFs cannot be easily enhanced after creation to support new interactive functionality.

Furthermore, conventional PDFs do not support in-document execution of interactive services. When a PDF includes links to audio, recorded or streaming video, video conferencing, reports, or other interactive content, selection of such links typically causes the PDF to invoke an external browser tab, media player, or third-party application. The interactive content therefore executes outside the PDF rather than within the document itself. In this model, the PDF serves only as a static container or launch point, and not as an environment in which communication, multimedia rendering, or data interaction can occur.

Because of these limitations, existing PDF technologies fail to provide a mechanism by which an existing or newly generated PDF can be enhanced, after creation. Existing solutions require proprietary authoring software, external platforms, or application launches, and do not allow multimedia content, reports, charts, communication interfaces, or functional services to operate as part of the PDF itself.

Accordingly, there exists a need for a system that enables post-creation insertion of links and interactive elements into PDF documents using an editor that operates independently of proprietary PDF authoring software, and that causes such links and elements to execute within the PDF itself as a real-time, network-connected interactive environment. There further exists a need for a system that preserves the portability and visual fidelity of a PDF while enabling in-document execution of communication, multimedia playback, structured data interaction, and functional services without requiring browser plugins, extensions, or external applications. This method of running services like chat and video conferencing on top of a PDF provides enormous value to its users. In the case of a PDF containing a brochure about a book, for example, the ability to instantly connect with the author of the book or a staff member of the book publishing company and ask about the book or even order it, right from the brochure, is priceless.

SUMMARY OF THE INVENTION

This application is a Continuation-in-Part (CIP) of U.S. patent application Ser. No. 17/084,850, the entirety of which is incorporated herein by reference. The system, methods, server architecture, execution model, link-based activation mechanism, and network-connected interactive PDF runtime disclosed in the parent application remain unchanged in this CIP. Both applications disclose the same core technology: a LivePDF system in which a portable document format (PDF) is activated by a link and executes as a real-time, browser-based, network-connected interactive environment without requiring plugins, extensions, or installed software.

The present CIP does not introduce a new document runtime, communication engine, or execution protocol. Instead, it extends the parent disclosure by adding an editor layer and explicitly describing additional supported interactive content types and document-linking capabilities that operate using the same underlying technology disclosed in patent application Ser. No. 17/084,850. The present invention clarifies that the core problem addressed is not merely linking from a PDF, but the inability of conventional PDFs to support reliable post-creation insertion of executable links and interactive content, particularly when the PDF is already generated, encrypted, or authored without proprietary tools such as Adobe Acrobat. The invention expressly relies on the same underlying execution technology disclosed in the parent patent application Ser. No. 17/084,850, and does not introduce a new runtime or platform; rather, it adds an editor-based mechanism that enables links, data, and interactive elements to be inserted into any existing PDF after creation while causing the PDF to execute identically to a LivePDF generated from scratch. The interactive elements supported by LivePDF, including audio, video, reports, charts, animated images, and other functional components, execute directly inside the document itself as part of the LivePDF environment, without opening new browser tabs, invoking external applications, or launching third-party software. Certain content types, such as GIF, SVG, and optionally audio, may execute automatically upon document load without requiring user selection of a link. This in-document execution model, combined with post-creation link insertion using the same technology as the parent application, distinguishes the invention from conventional PDFs that merely launch external services and ensures continuity with the previously granted parent patent/patent application Ser. No. 17/084,850.

Definition

LivePDF or LivePDF system refers to a link-activated, interactive portable document format (PDF) that executes as a real-time, network-connected application environment within a browser context, rather than as a static document. A LivePDF is generated from scratch or by enhancing an existing PDF and is activated by a selectable link that launches the document without requiring installation of software applications, browser extensions, plugins, or external viewers. Upon execution, the LivePDF functions as a runtime container that integrates content, communication, data exchange, and executable services directly within the document interface. A LivePDF supports, within the document itself, one or more of: real-time chat, audio communication, and video communication; interactive forms and structured data capture; spreadsheet-like data tables with searching, sorting, filtering, and dynamic chart generation; inline playback of multimedia content including video, animated images, and audio; execution of embedded micro-tools that provide task-specific services such as database search, lookup, calculation, scheduling, or transactions; and chaining of multiple LivePDF documents through links that launch additional LivePDFs while preserving interactivity. A LivePDF operates using a server-based execution and communication architecture and produces a technical effect by transforming a conventional static PDF into a real-time, browser-accessible, network-connected execution environment. The LivePDF maintains the visual fidelity and portability of a PDF while enabling dynamic interaction, collaboration, and service execution directly within the document. As used herein, LivePDF does not denote a new file format or viewer, but rather a system and method for activating and executing an interactive PDF using the same underlying document format and execution technology disclosed in U.S. patent application Ser. No. 17/084,850. In other words, LivePDF is a link-activated portable document format (PDF) that executes within a browser as a real-time, network-connected interactive environment, integrating multimedia, structured data, communication, and executable services directly within the document without requiring plugins, extensions, or installed software.

The present invention discloses a system for providing interactive portable document format (PDF) document. The system comprises a server, a database in communication with the server, one or more user device associated with the user. The server, the database and the user device are in communication with one another via a network.

The server comprises a processor and a memory storing a set of instructions executable by the processor. The instructions comprising a software module. In one embodiment, the software module comprises a document generation and execution module, an instant communication module, a link generation module and a link detection and processing module. The document generation and execution module is configured to generate an interactive portable document format (PDF) via the user device associated with the user and connected to the server. The interactive PDF comprises multimedia content including images, animations, and video streams. The document generation and execution module is further configured to execute or inject the interactive portable document format (PDF) over a web application executed in a browser environment.

The instant communication module is configured to integrate and display one or more interfaces of one or more Enterprise Messaging Network services over the interactive PDF. The instant communication module is configured to enable real-time communication, including video conferencing and messaging, between users via the Enterprise Messaging Network services. A cross-domain configuration framework, implemented on the server, enables secure and permissioned interaction of the system with external websites, third-party applications, and social media platforms while maintaining compliance with healthcare data privacy requirements. Upon user interaction with the displayed interface, the system activates HIPAA-compliant, enterprise-grade content messaging and chat, forms, scheduling, and live video conferencing features.

The link generation module is configured to generate a unique uniform resource locator (URL) identifying the generated interactive PDF. The link detection and processing module is configured to detect links and determine whether such links are associated with a live network of live network server or system. Upon detecting the link associated with the live network server, the system is configured to execute one or more services on top of the application, execute one or more services on top of the interactive PDF document or execute the interactive PDF on top of the application based on the detected link. The services include multimedia content images, animations, video streams and execution of embedded interfaces.

In one embodiment, the document generation and execution module is configured to generate the interactive portable document format (PDF) from scratch or by enhancing existing PDFs. The document generation and execution module is further configured to provide one or more options to create the interactive portable document format, including a text option configured to add, edit, or remove text within the interactive PDF, an image option configured to add or remove images within the interactive PDF, a shape option configured to add or manipulate graphical shapes within the interactive PDF, and a free-drawing option configured to enable freehand drawing within the interactive PDF. The document generation and execution module further provides a video embedding option configured to embed video content, including third-party video sources, within the interactive PDF, and an audio option configured to embed audio content within the interactive PDF. The document generation and execution module further provides a report option configured to add or generate report content within the interactive PDF, a form option configured to add interactive forms within the interactive PDF, a link option configured to embed selectable hyperlinks within the interactive PDF, and an upload option configured to enable file uploads within the interactive PDF.

In one embodiment, the generated interactive PDF is embedded with one or more embedded interfaces. The embedded interfaces include a communication interface configured to enable real-time chat, audio communication, and video conferencing within the interactive PDF, a payment processing interface configured to enable payment transactions within the interactive PDF, and a scheduling interface configured to enable appointment scheduling within the interactive PDF. The embedded interfaces further include a database lookup interface configured to enable querying and retrieval of data from one or more databases within the interactive PDF, and a media playback interface configured to provide text-to-speech, recorded audio playback, and inline media playback within the interactive PDF. The embedded interfaces further include a chart generation interface configured to dynamically create one or more charts by selecting data provided within the interactive PDF. The chart generation interface is further configured to enable a user to search, filter, and rearrange columns of data provided within the interactive PDF and to dynamically generate one or more charts based on the selected data.

In one embodiment, execution of the live, interactive PDF produces a technical effect by transforming a static document into a real-time, network-connected execution environment for data management, secure communication, multimedia rendering, and structured data exchange.

In one embodiment, the Enterprise Messaging Network services include a live video conferencing service, an instant messaging and notifications service, a group messaging service, and a direct file sharing service. The instant communication module is bi-directional and configured to enable the Enterprise Messaging Network to communicate with other users. The user devices, the Enterprise Messaging Network, and the server are in communication via a communication network.

In one embodiment, the Enterprise Messaging Network device includes one or more computing devices with computational capability connected to the network. The user devices are at least one of a tablet computer, personal computer, personal digital assistant, smart phone, smart television, palm-top device, phablet, laptop, or another device with computational capability connected to the network.

In one embodiment, the server further includes a portal software module executed by the processor, wherein the portal software module is configured to provide users with an interface to generate the interactive PDF. In one embodiment, the interactive PDF is accessible through a uniform resource locator (URL) and launches instantly without requiring installation of software applications, browser extensions, or plugin components.

In one embodiment, the system further comprises an editor configured to facilitate authoring, insertion, and orchestration of interactive elements within a LivePDF document. The editor operates solely as a composition and configuration interface and does not alter the execution environment, runtime behavior, or communication architecture of the LivePDF system disclosed in the parent application.

In one embodiment, the interactive PDF further supports animated image formats including GIF and SVG images that automatically render and animate inline within the document upon execution.

In one embodiment, the interactive PDF supports spreadsheet-like structured data tables derived from external applications or uploaded spreadsheet files, including Excel-compatible formats, without requiring Microsoft Office or third-party spreadsheet software. The tables support searching, sorting, filtering, column rearrangement, selection of rectangular data ranges, and dynamic generation of charts based on the selected data.

In one embodiment, the interactive PDF supports embedded audio playback including MP3 audio files that play directly within the document interface without launching external media players.

In one embodiment, the interactive PDF embeds executable micro-tools that function as lightweight, task-specific applications activated by selectable links within the document. The micro-tools execute within the LivePDF environment and provide services including database search, calculation, lookup, scheduling, or transactional operations. In one example, a document related to diabetes enables execution of a nutrition database micro-tool that searches hundreds of thousands of food records to retrieve sugar content, vitamin data, and mineral information.

In one embodiment, the interactive PDF supports document chaining, wherein activation of a link within a first LivePDF document launches a second LivePDF document, enabling construction of multi-document books, lesson plans, training courses, or modular content systems while preserving full interactivity within each document.

The execution of the interactive PDF produces the same technical effect disclosed in the parent application, namely, transforming a static PDF into a real-time, network-connected execution environment, while further enhancing multimedia rendering, structured data interaction, micro-service execution, and multi-document orchestration using the same core technology.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The embodiments herein will be better understood from the following detailed description with reference to the drawings, in which.

document displaying video content, according to an embodiment of the present invention.

Figure 6:
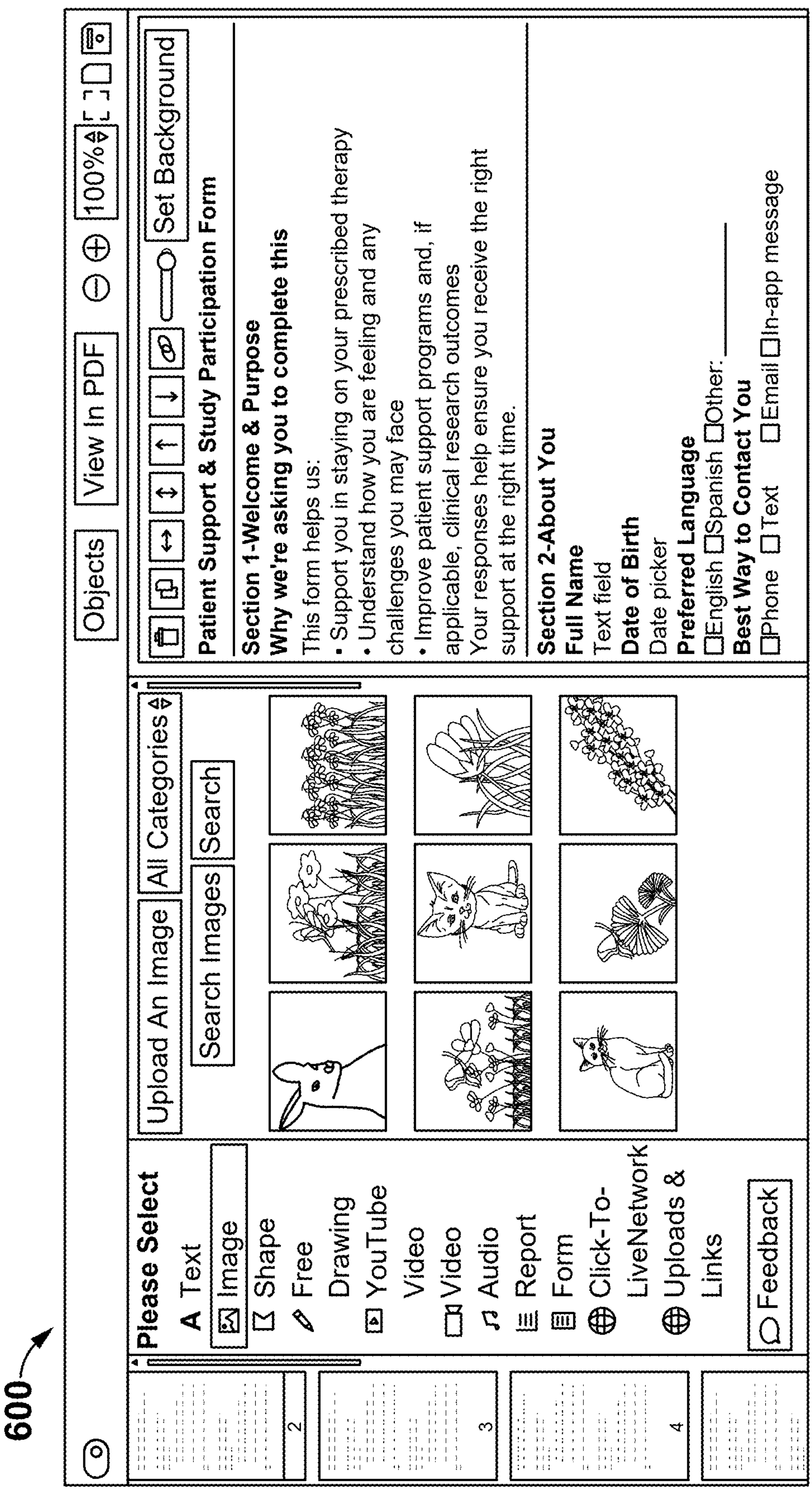

FIG. 6 exemplarily illustrates a screenshot of a user interface comprising one or more options to create the interactive PDF, according to an embodiment of the present invention.

Figure 7:
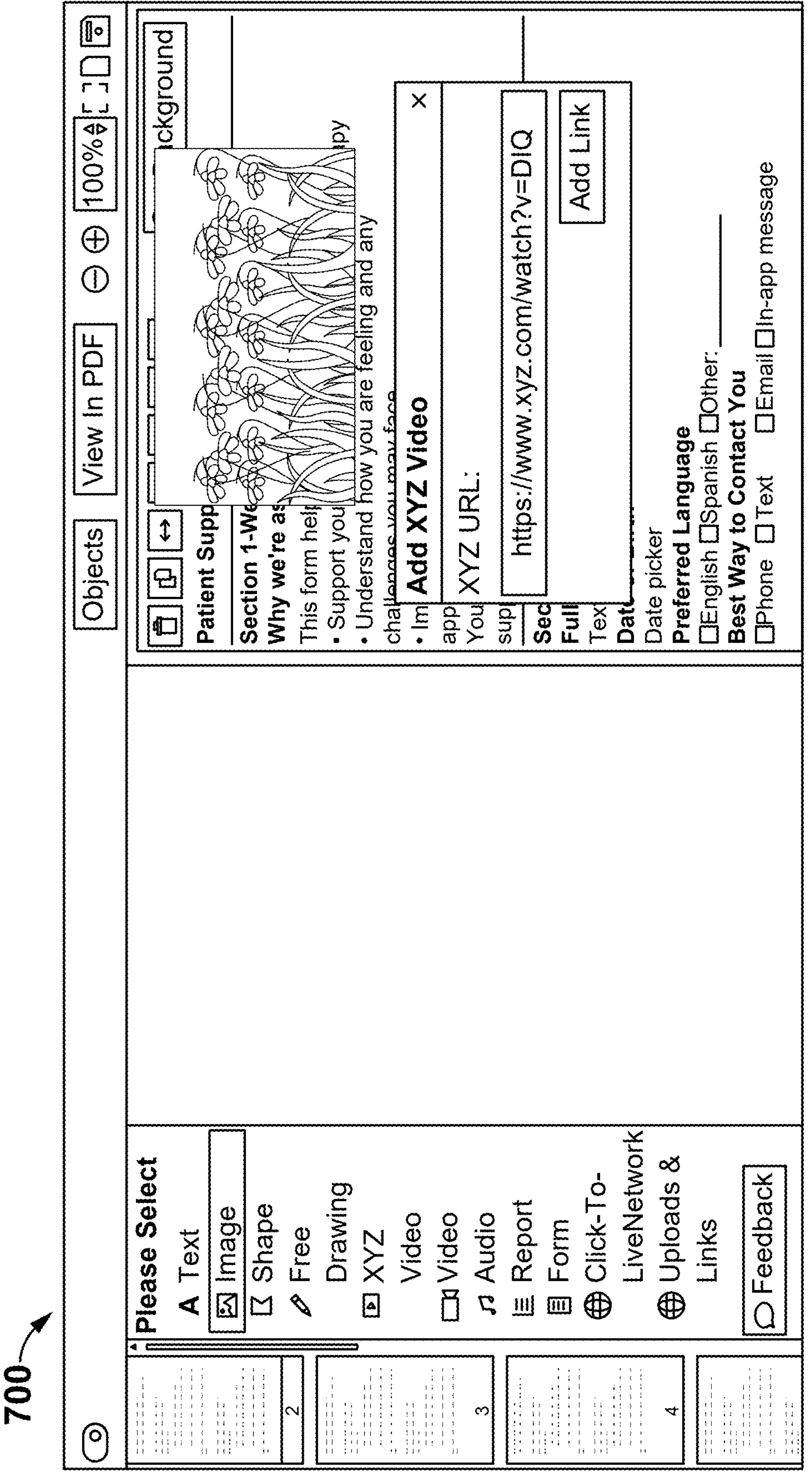

FIG. 7 exemplarily illustrates a screenshot of a user interface to add a video in the interactive PDF, according to an embodiment of the present invention.

Figure 8:
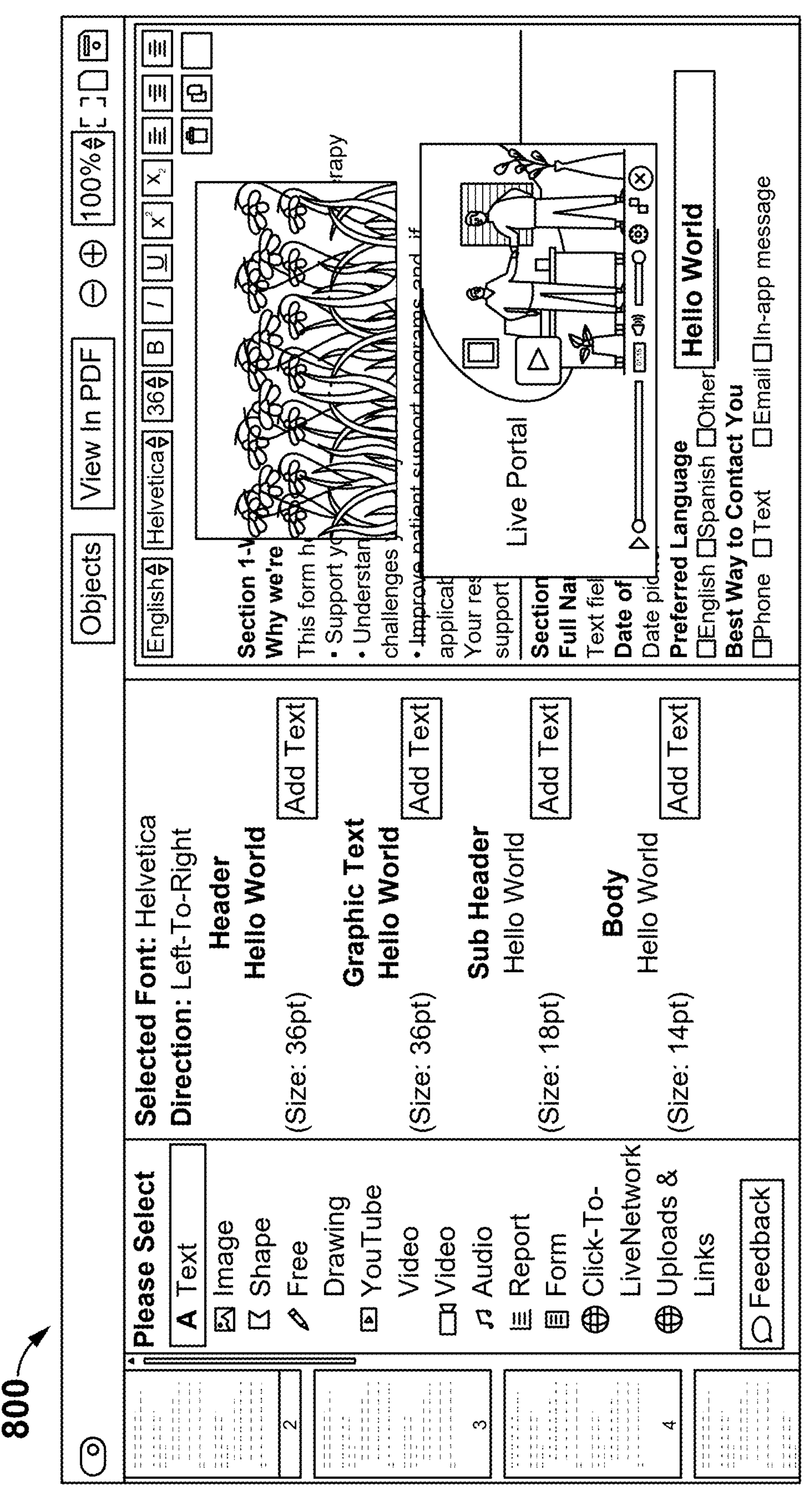

FIG. 8 exemplarily illustrates a screenshot of a user interface to add text with a hyperlink to the interactive PDF, according to an embodiment of the present invention.

Figure 9:
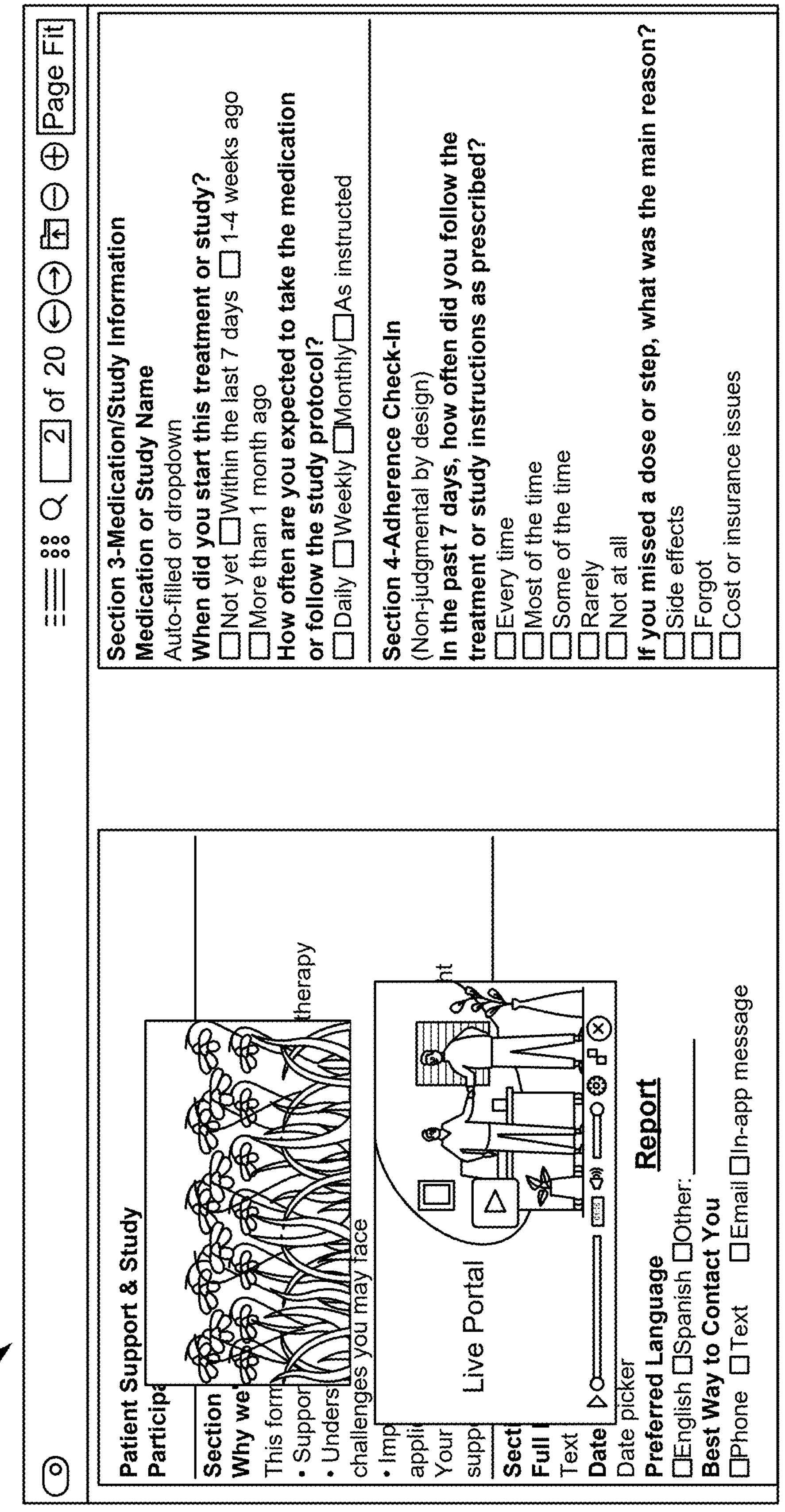

FIG. 9 exemplarily illustrates a screenshot of a user interface displaying the edited interactive PDF, according to an embodiment of the present invention.

FIG. 10 exemplarily illustrates a screenshot of a user interface displaying a report added with the text of FIG. 8 via the hyperlink, according to an embodiment of the present invention.

Figure 11:
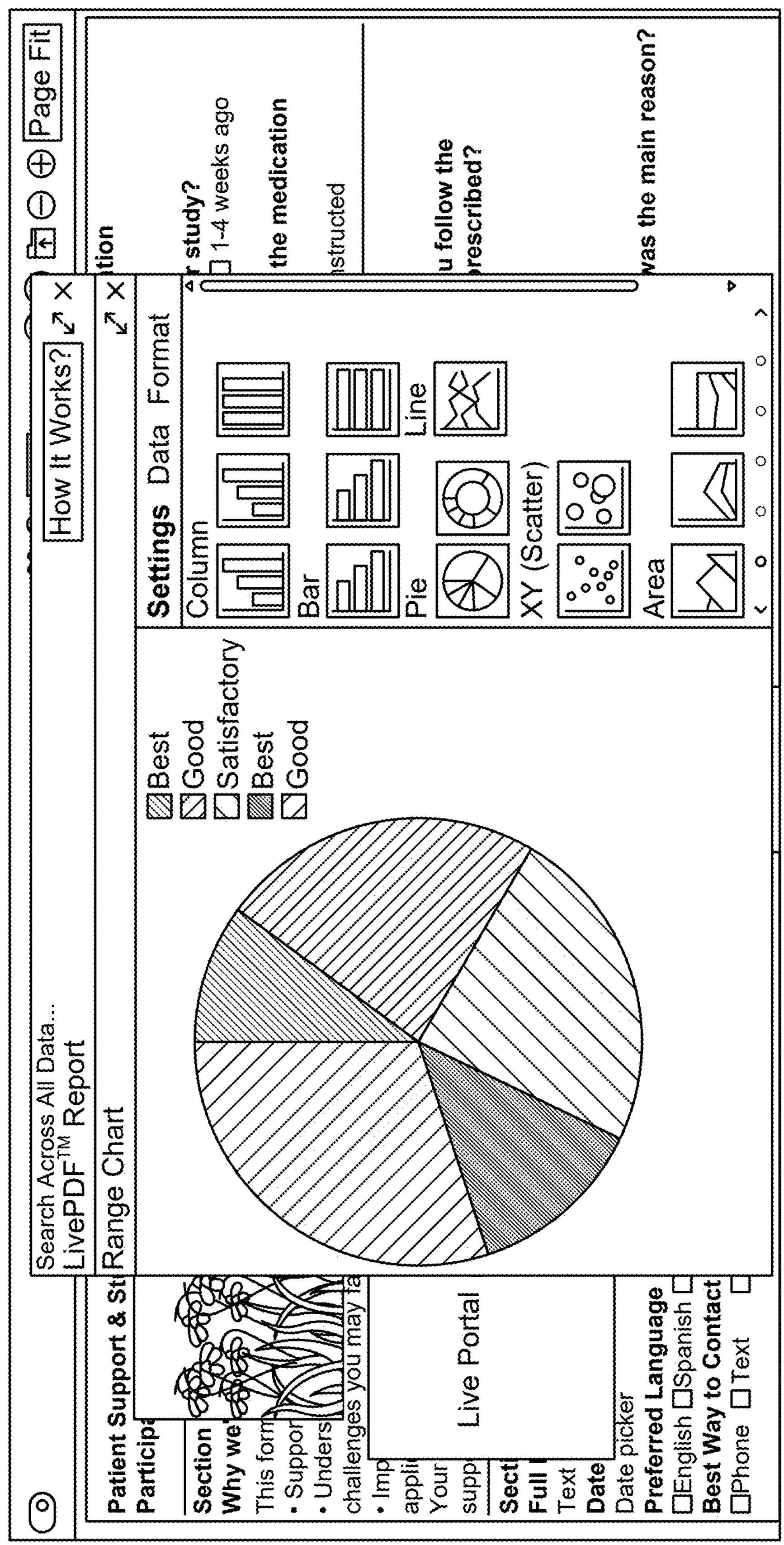
Figure 12A:
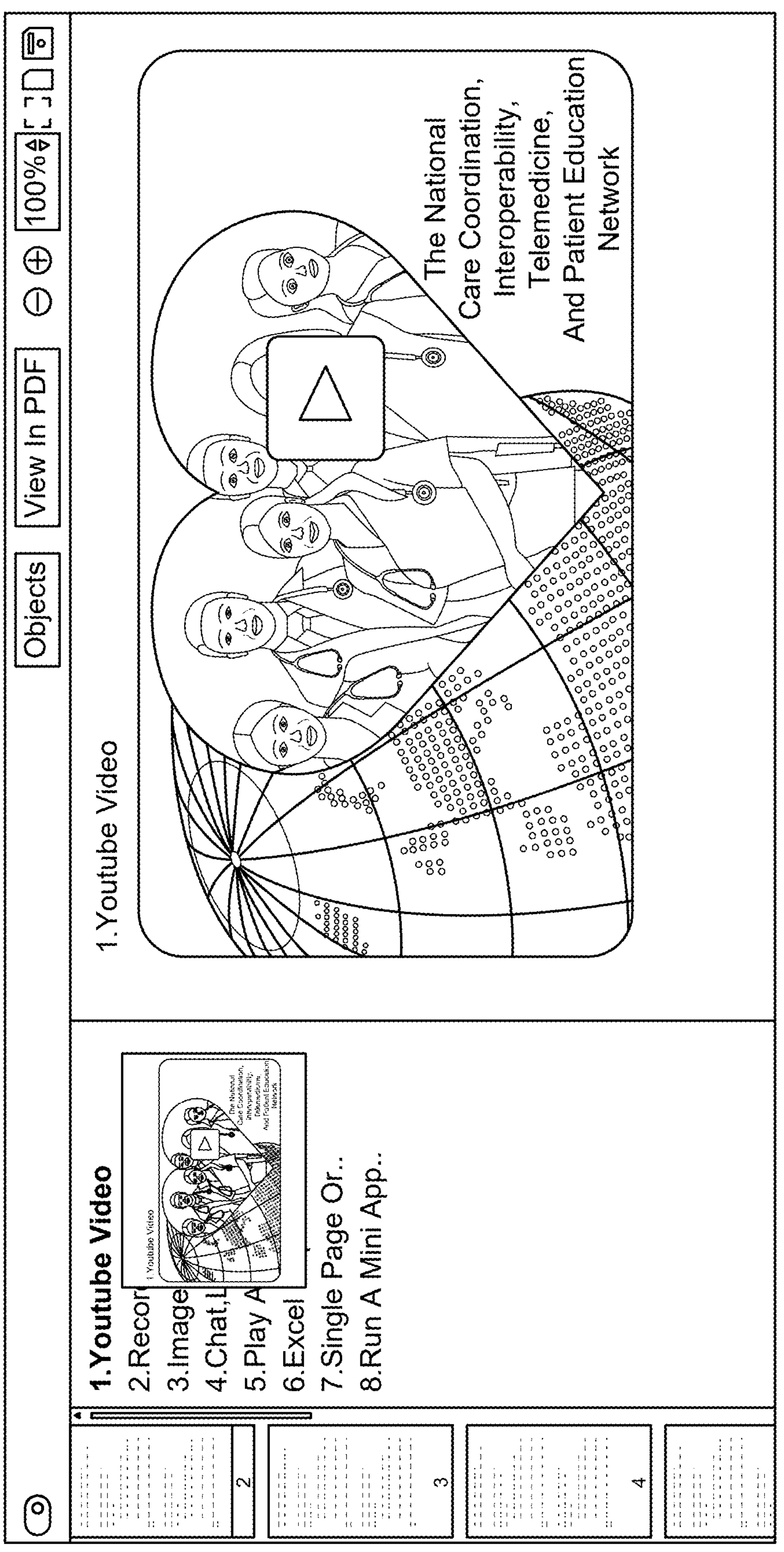
Figure 12B:
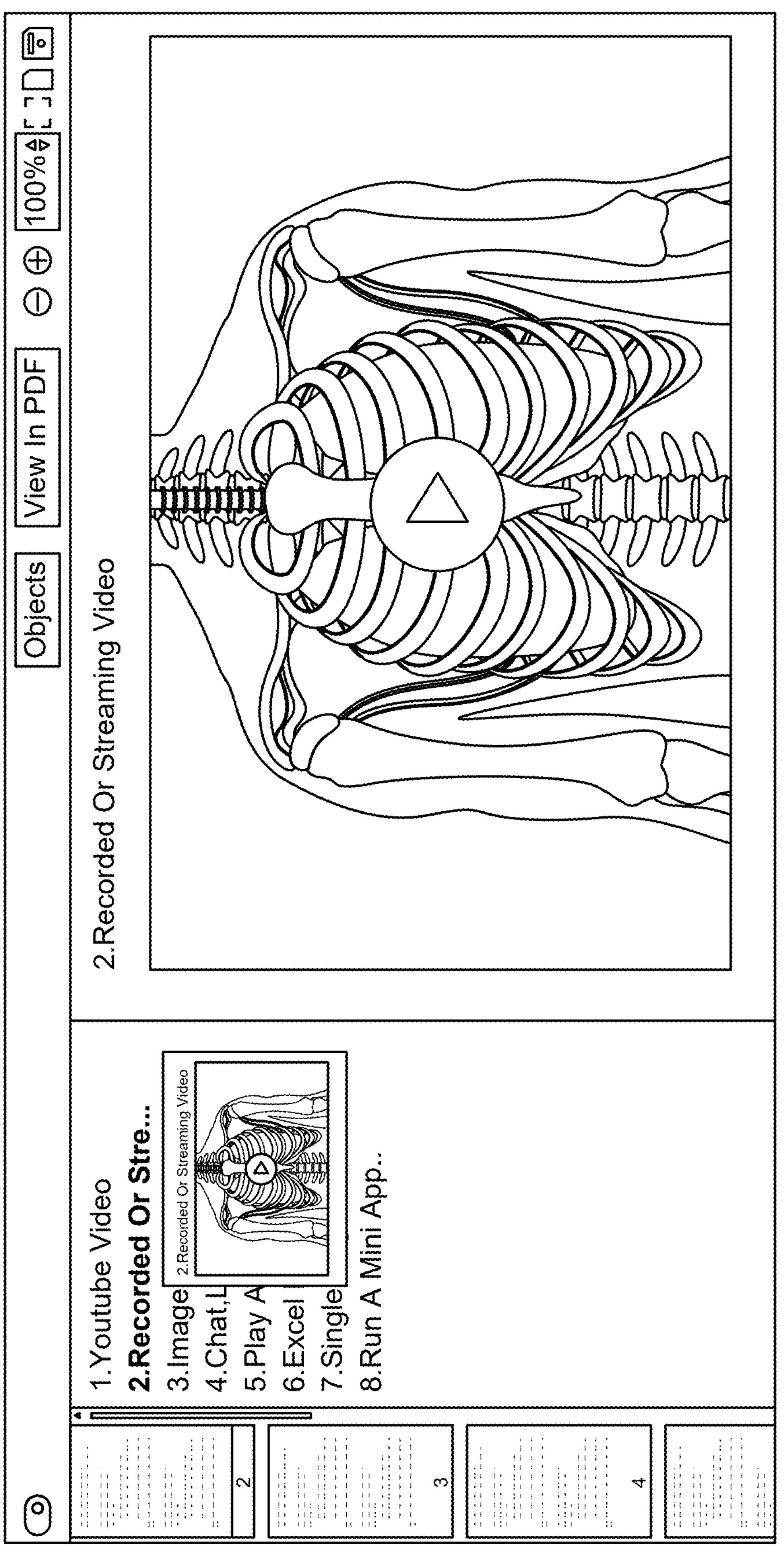
Figure 12C:
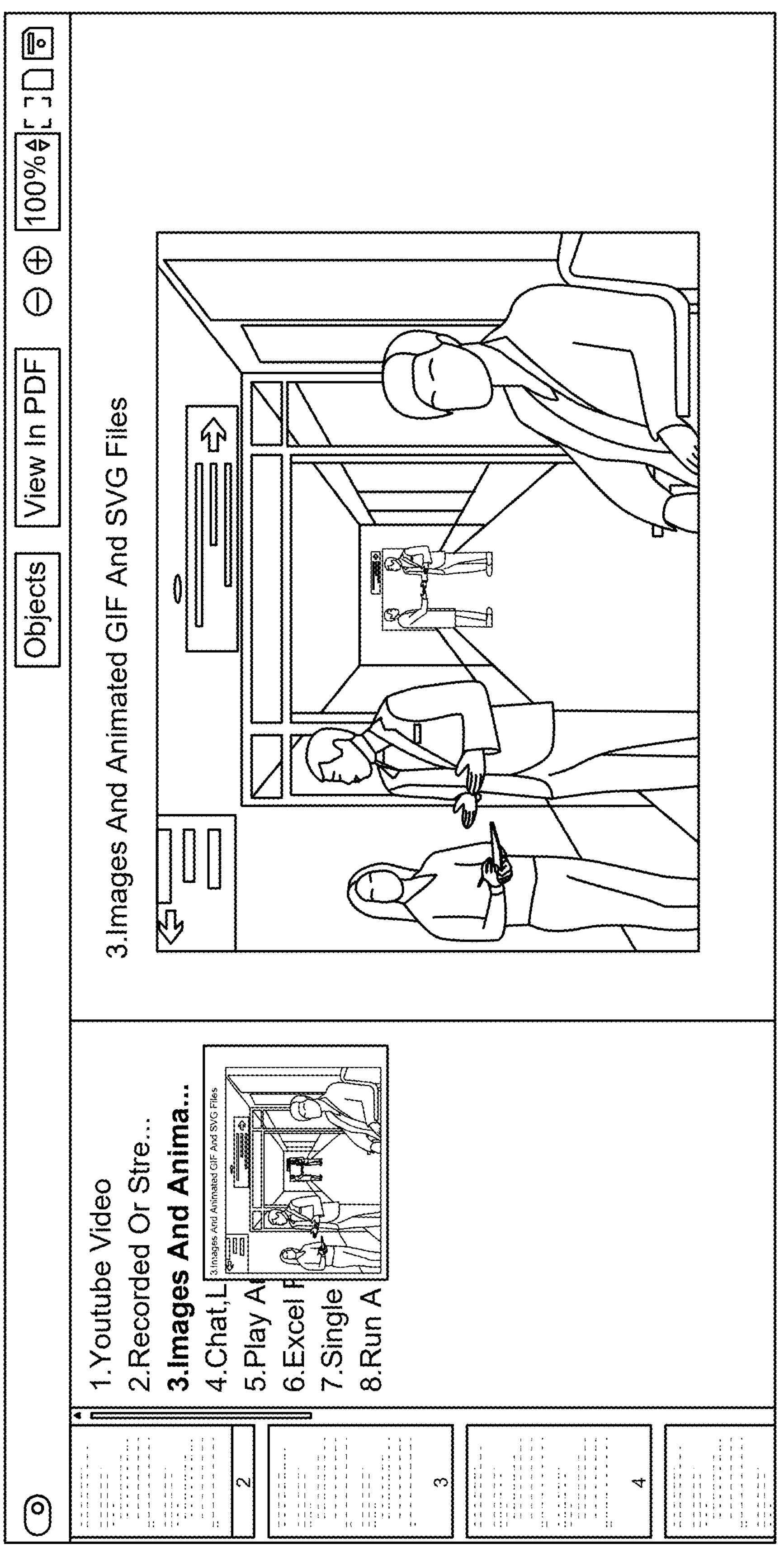
Figure 12D:
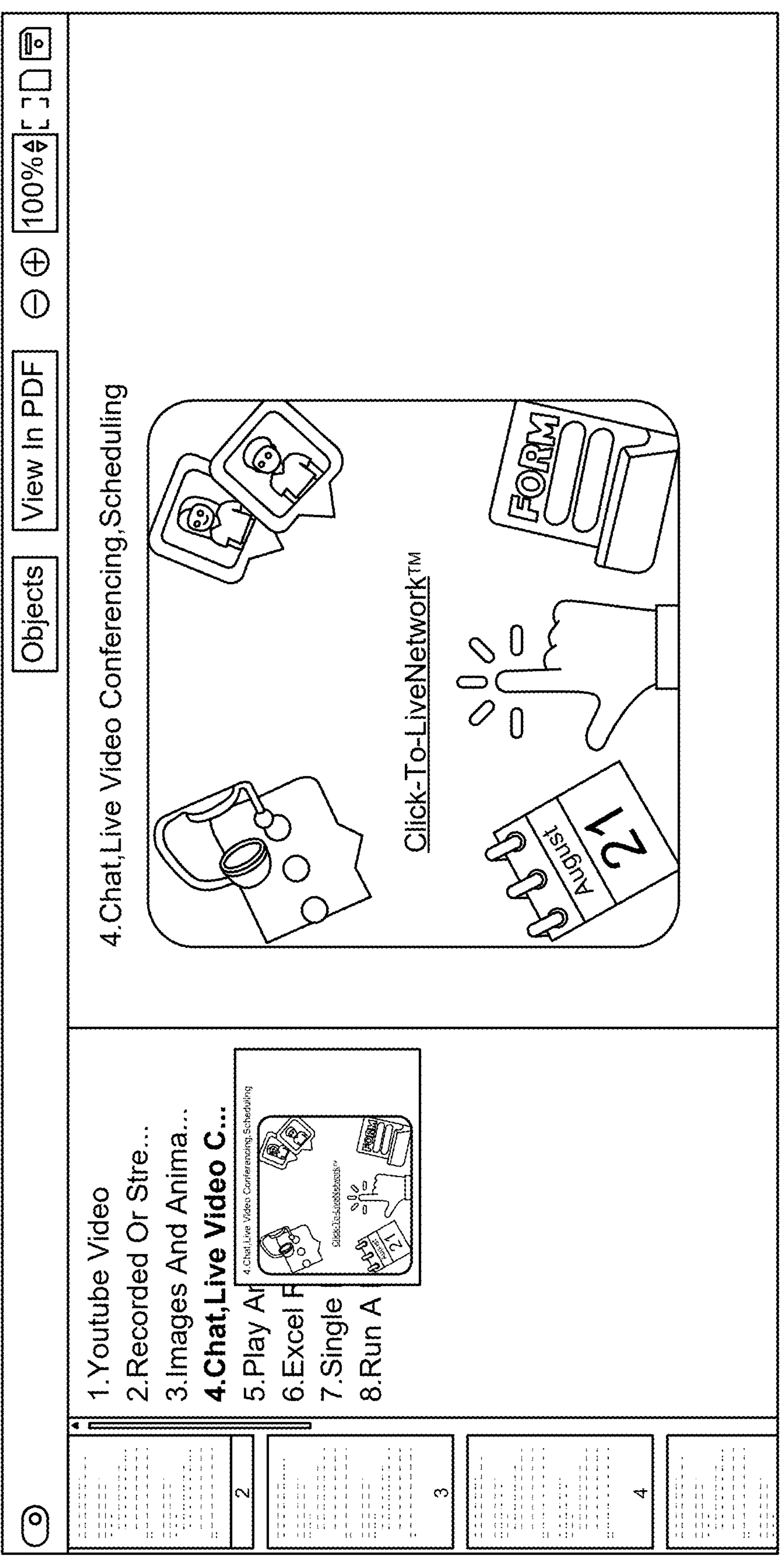
Figure 12E:
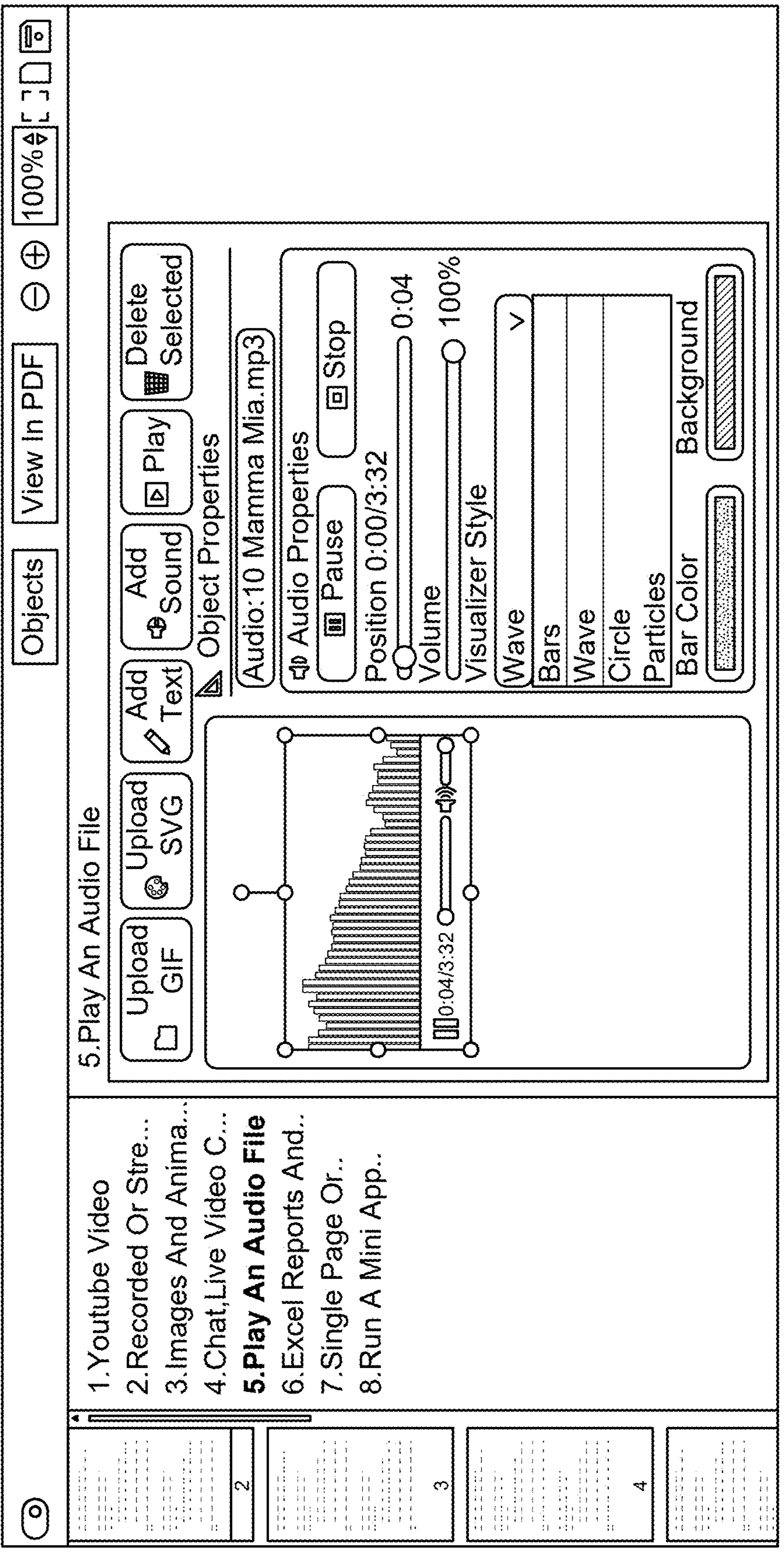
Figure 12G:
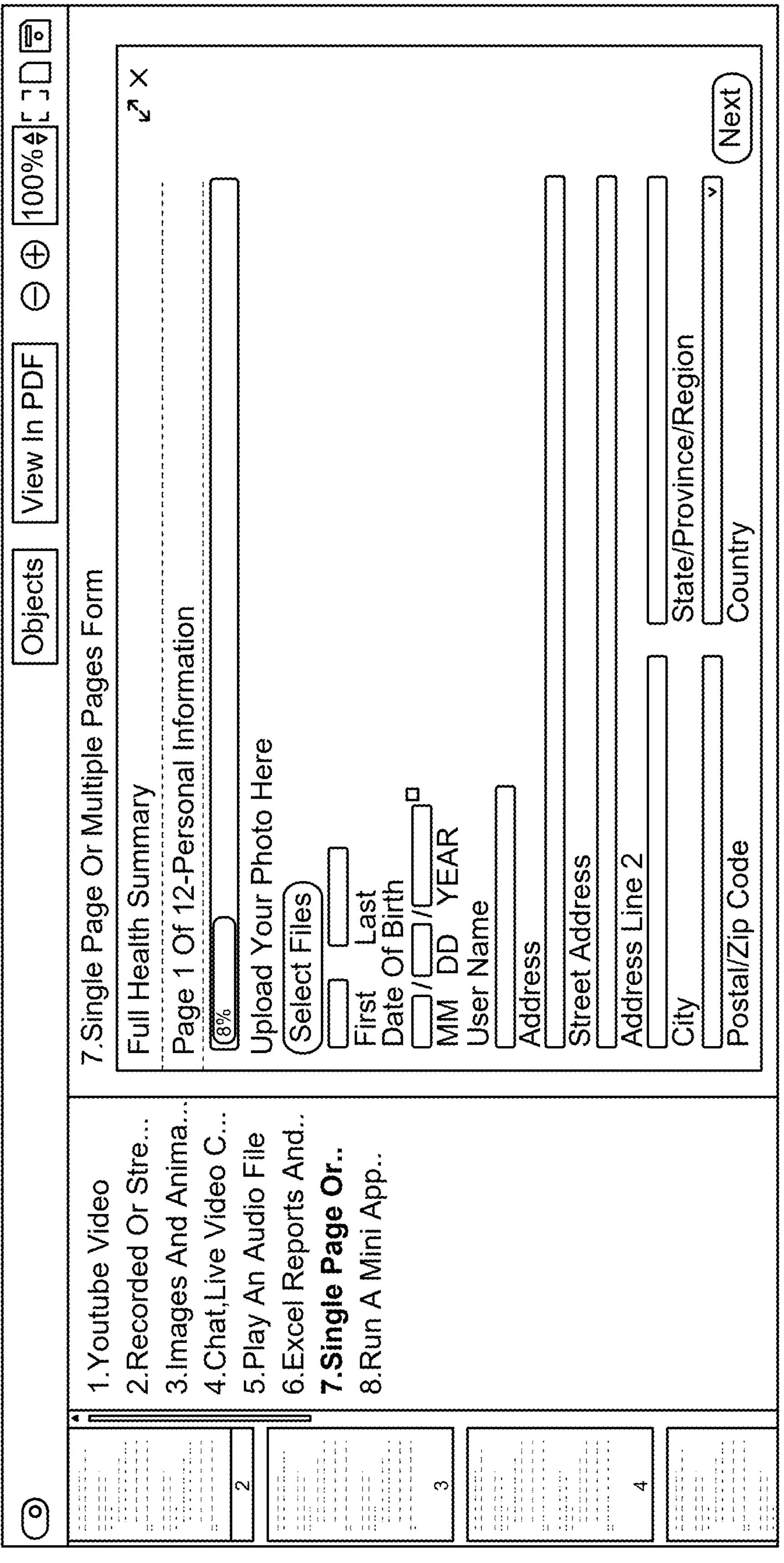
Figure 12H:
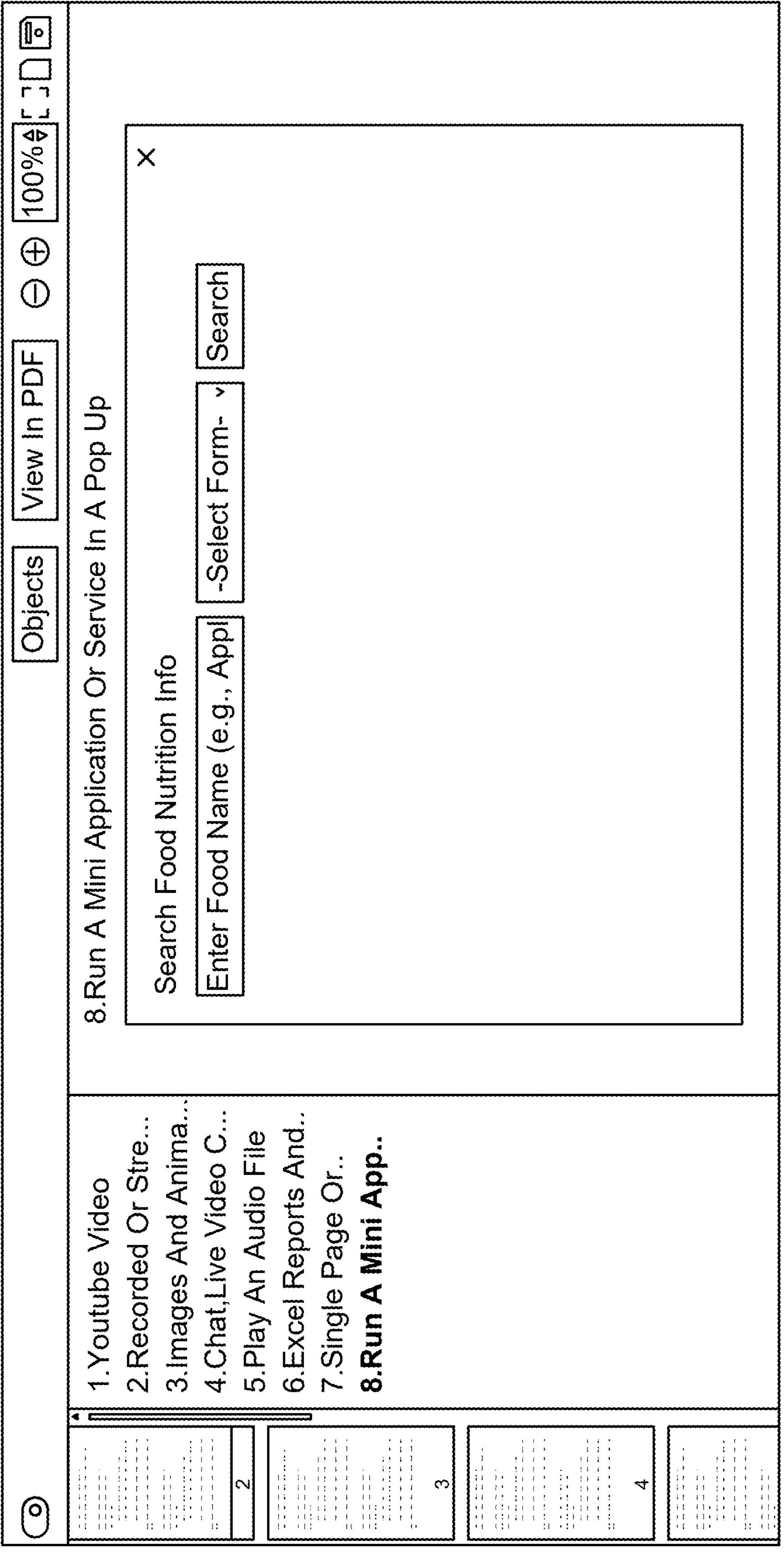
Figure 12I:
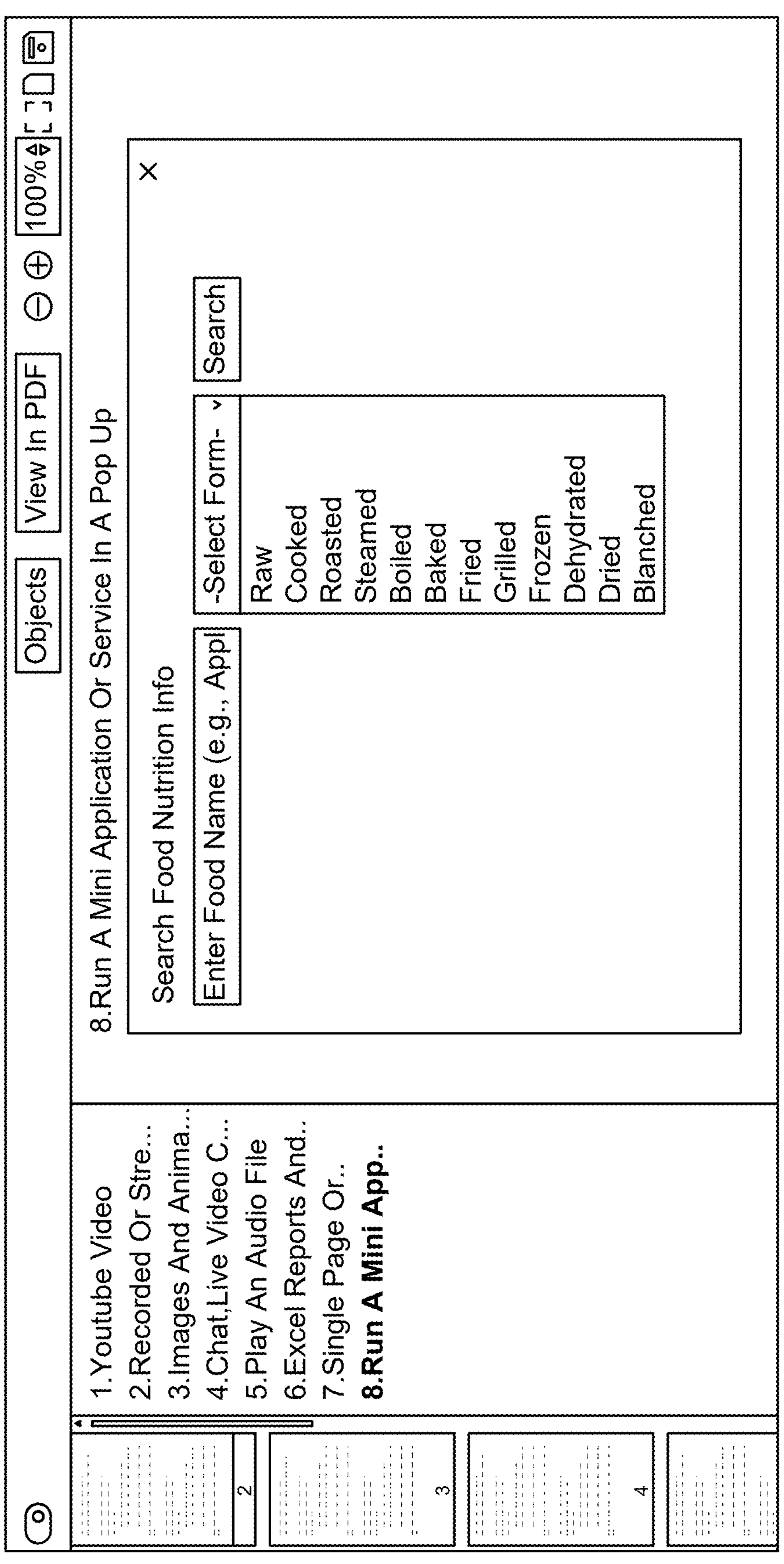
Figure 12J:
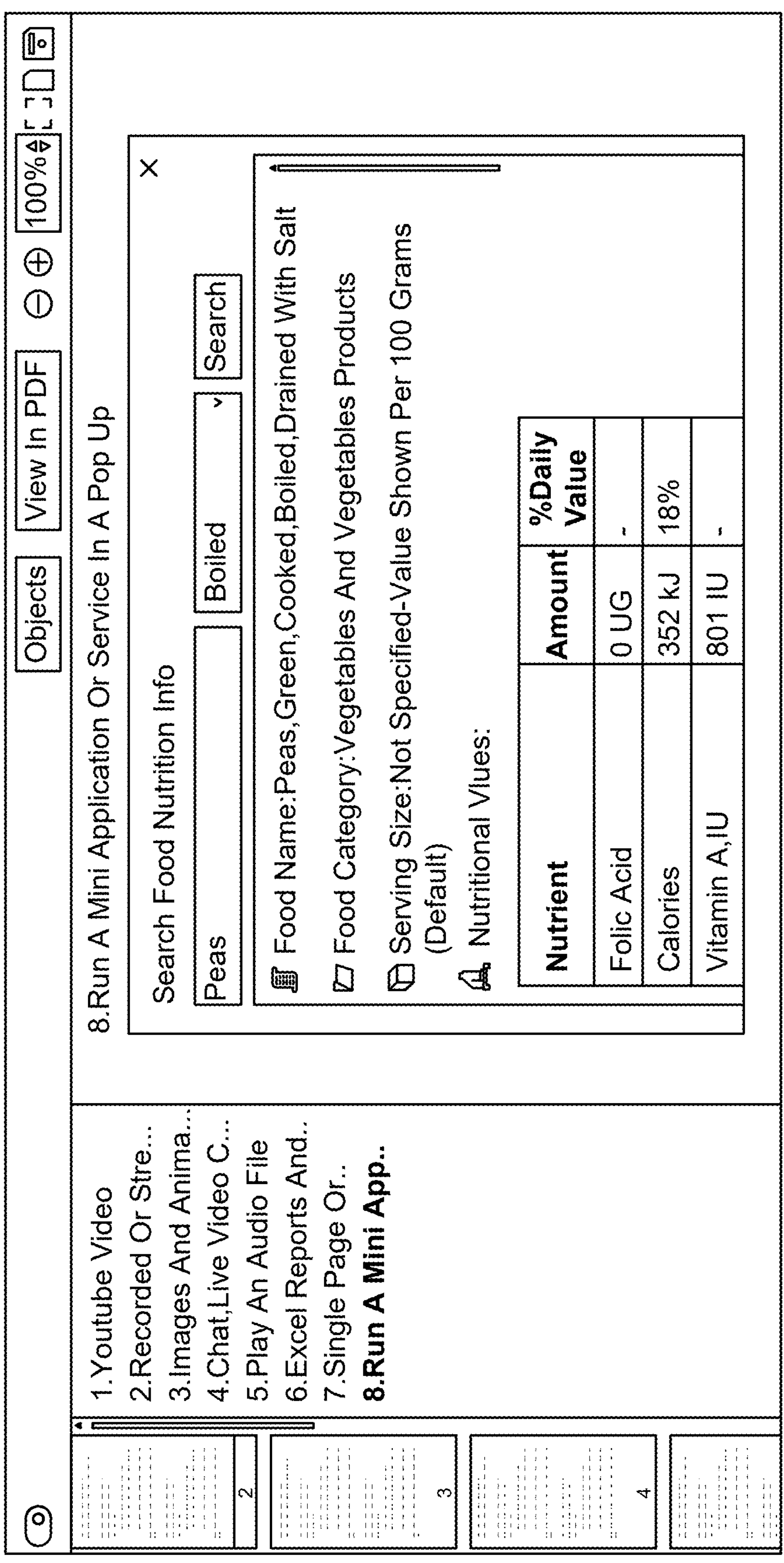

FIG. 11 exemplarily illustrates a screenshot of the interactive PDF displaying a pie chart generated from data of the report of FIG. 10 using the options provided within the interactive PDF, according to an embodiment of the present invention.

FIG. 12A-12J provides an example overview of all interactive items that can be added to an interactive PDF (LivePDF) document and demonstrated live. These include YouTube videos, recorded and streaming video, images, animated GIFs and SVGs, chat, live video conferencing and scheduling, audio playback, Excel reports and web-captured charts or tables, single- and multi-page forms, and the ability to run mini-applications or services in pop-up windows, transforming static PDFs into fully interactive experiences.

DETAILED DESCRIPTION OF EMBODIMENTS

The present invention clarifies that the core problem addressed is not merely linking from a PDF, but the inability of conventional PDFs to support reliable post-creation insertion of executable links and interactive content, particularly when the PDF is already generated, encrypted, or authored without proprietary tools such as Adobe Acrobat. The invention expressly relies on the same underlying execution technology disclosed in the parent patent application Ser. No. 17/084,850, and does not introduce a new runtime or platform; rather, it adds an editor-based mechanism that enables links, data, and interactive elements to be inserted into any existing PDF after creation while causing the PDF to execute identically to a LivePDF generated from scratch. The interactive elements supported by LivePDF, including audio, video, reports, charts, animated images, and other functional components, execute directly inside the document itself as part of the LivePDF environment, without opening new browser tabs, invoking external applications, or launching third-party software. Certain content types, such as GIF, SVG, and optionally audio, may execute automatically upon document load without requiring user selection of a link. This in-document execution model, combined with post-creation link insertion using the same technology as the parent application, distinguishes the invention from conventional PDFs that merely launch external services and ensures continuity with the previously granted parent patent/patent application Ser. No. 17/084,850.

The present invention discloses a system for providing interactive portable document format (PDF) documents. The interactive PDF is provided with real-time communication interfaces and data management interfaces that enable real-time collaboration and data exchange within the PDF document without requiring a user to exit the document. The system is configured to execute or inject the interactive portable document format (PDF) over a web application executed in a browser environment. The interactive PDF refers to a digital document format configured to enable user interaction beyond static viewing, including but not limited to clicking hyperlinks, entering data into forms, communicating in real-time, generating and updating charts, viewing multimedia content, and performing operations such as copy, paste, or export, all without exiting the PDF page or requiring external applications or plugins.

Figure 1:
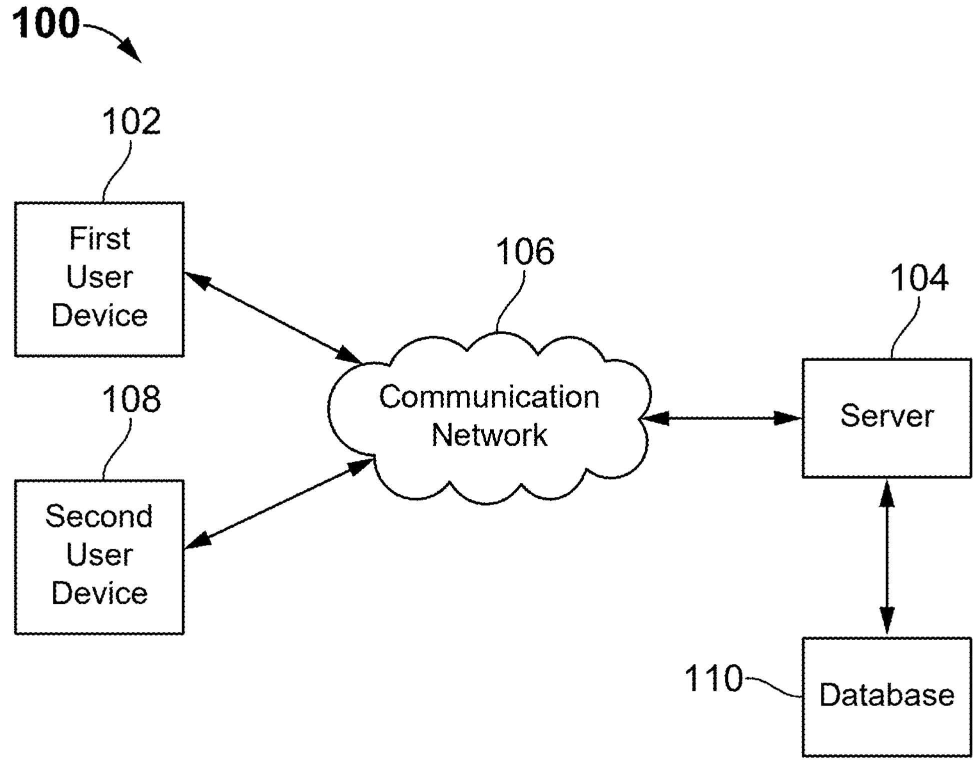
FIG. 1 exemplarily illustrates an environment of a system for providing an interactive portable document format (PDF) document, according to an embodiment of the present invention.

Referring to FIG. 1, the environment 100 includes a first user device 102, a second user device 108, one or more servers, such as server 104, and a database 110, each coupled directly or indirectly to a communication network 106.

In one embodiment, the database 110 is accessible by the server 104. The database 110 may be integrated with the server 104 or operate as a separate component. In some embodiments, the database 110 resides within the server 104 or within a cloud computing environment. Regardless of location, the database 110 comprises memory configured to store and organize data for use by the server 104.

In an embodiment, the communication network 106 includes one or more of a Wi-Fi network, WiMAX network, wireless local area network, or other communication networks. In one embodiment, the server 104 comprises at least one general-purpose or special-purpose computing device. The server 104 may operate as a single computing system or as a distributed computing system, including one or more servers, workstations, desktops, laptops, tablets, mobile devices, or other computing devices capable of network communication. The computing devices may operate using touchscreen or non-touchscreen interfaces and execute operating systems including iOS™, Windows™, Android™ Linux™, Unix™, or combinations thereof.

Figure 2:
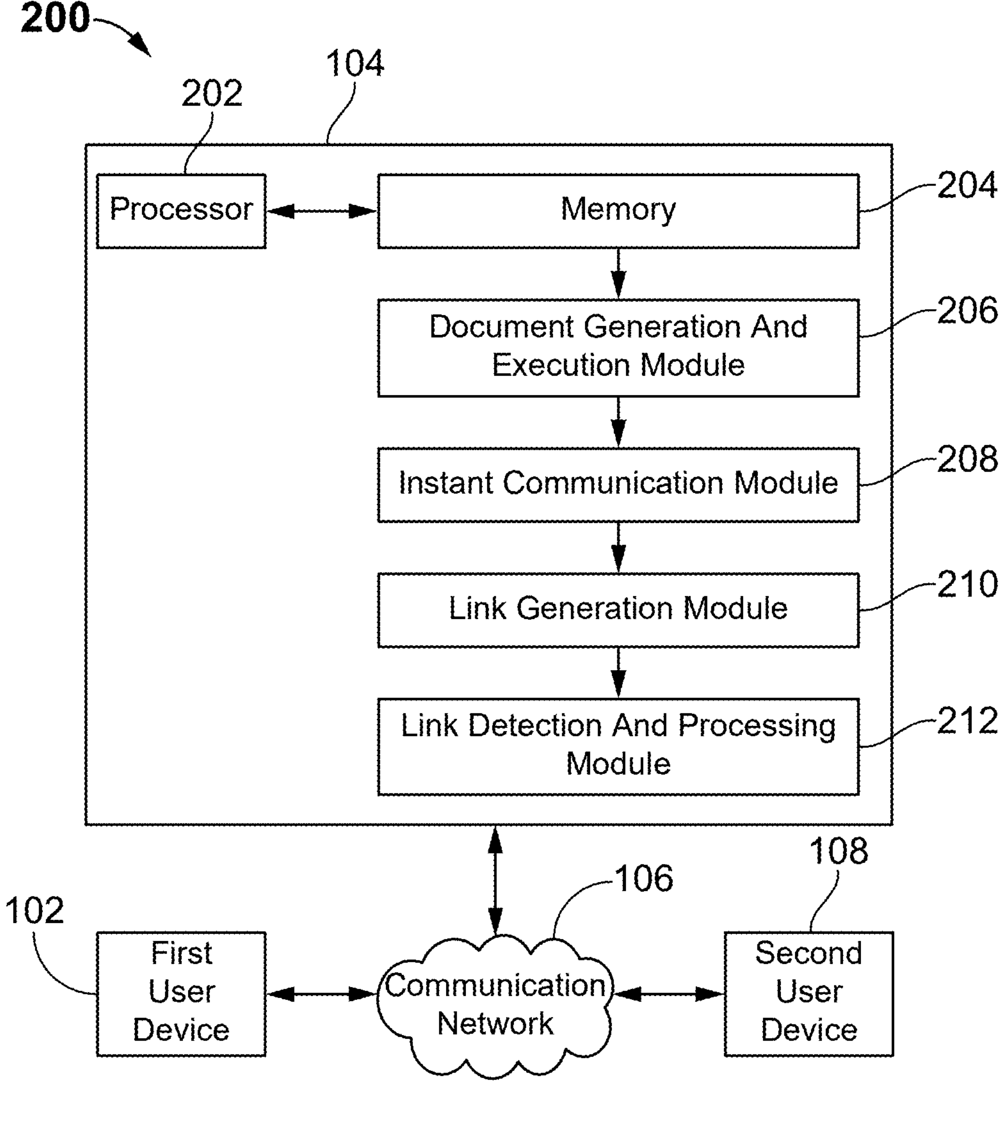
FIG. 2 exemplarily illustrates a block diagram of a server, according to an embodiment of the present invention.

Referring to FIG. 1 and FIG. 2, in one embodiment, the server 104 includes one or more software modules executed by a processor 202, including a document generation and execution module 206, an instant communication module 208, a link generation module 210, and a link detection and processing module 212, as described herein.

The first user device 102 and the second user device 108 could be any type of electronic device that provides one or more services or functions to a user.

The first user device 102 is associated with a first user. In one embodiment, the first user device 102 is configured as at least one of a desktop computer, laptop, tablet, smartphone, or other handheld or computing device. The first user device 102 includes an operating system configured to manage hardware and software resources and one or more applications, including a web browser or web application, capable of accessing the server 104 via the communication network 106. In one embodiment, the first user generates or publishes a link associated with an interactive portable document format (PDF) document.

The second user device 108 is associated with a second user. In one embodiment, the second user device 108 is configured as at least one of a desktop computer, laptop, tablet, smartphone, or other computing device. The second user device 108 includes an operating system and one or more applications, including a web browser, configured to access the interactive PDF via the communication network 106. In one embodiment, the interactive PDF is accessed through a link and executed without requiring installation of software applications, plugins, or browser extensions.

In one embodiment, the first user refers to any individual or entity that generates or shares a link associated with the interactive PDF through a web application, website, or digital platform. The second user refers to any individual or entity that accesses the link and opens the interactive PDF using the second user device 108.

In one embodiment, the server 104 enables real-time interaction between the first user device 102 and the second user device 108 through the interactive PDF. The system enables communication, including messaging, audio communication, video communication, scheduling, and data exchange, to occur directly within the interactive PDF while the users remain within the same document interface. The interactive PDF further enables updating of content including text, images, links, and embedded interfaces without requiring the users to exit the document.

In one embodiment, upon a user selecting or activating one or more embedded interfaces within the interactive PDF, the system initiates real-time communication, data collection, scheduling, or multimedia interaction between the first user device 102 and the second user device 108. The system enables users to respond to communications, invite additional participants, or transition between messaging and live communication modes without leaving the interactive PDF or accessing a separate application.

As used herein, the first user and the second user are collectively referred to as users, the first user device 102 and the second user device 108 are collectively referred to as user devices (102, 108), and any function, operation, or interaction described herein may be performed by any user via any user device (102, 108) without limitation.

The server 104 is configured to generate and execute interactive portable document format (PDF) documents, referred to herein as LivePDF™, from scratch or by enhancing existing PDF documents. The interactive PDFs are configured to function as real-time, network-connected execution environments rather than static documents.

The server 104 is further configured to enable embedding, presentation, and execution of real-time communication features directly within the interactive PDF, including live chat, group chat, audio communication, recorded audio, live video conferencing, and embedded third-party video content, including streaming video sources.

The server 104 is further configured to enable interactive data exchange within the interactive PDF, including interactive forms, structured data capture, report generation, spreadsheet-based data uploads, direct data entry, searching, filtering, rearranging data columns, and dynamically generating charts and dashboards from data provided within the interactive PDF.

The server 104 is further configured to embed and execute functional micro-tools within the interactive PDF, including payment processing, order placement, scheduling, database lookup, search utilities, calculators, and transaction execution. The micro-tools operate without requiring installation of software applications, browser extensions, or plugin components. The server 104 is further configured to detect links and determine whether such links are associated with live network server. upon detecting the link associated with the live network server 104, the system is configured to execute one or more services on top of the application, execute one or more services on top of the interactive PDF document or execute the interactive PDF on top of the application based on the detected link. The services include multimedia content images, animations, video streams and execution of embedded interfaces or micro tools.

The server 104 is further configured to enable secure content delivery and communication within the interactive PDF by encrypting content and maintaining controlled access to interactive features, including recording live video sessions conducted on top of the interactive PDF or a user desktop.

The server 104 is further configured to provide a document editing environment enabling creation and modification of interactive PDFs using selectable options including text, images, shapes, free drawing, audio, video, reports, forms, hyperlinks, uploads, and multimedia content, and to provide access to a library of high-quality, royalty-free images.

The server 104 is further configured to enable search functionality within the interactive PDF to locate content, data fields, or embedded media.

The server 104 is further configured to support use of the interactive PDF across multiple application domains, including but not limited to brochures, portfolios, books, research papers, employee handbooks, educational materials, instruction manuals, contracts, reports, proposals, newsletters, meeting agendas, landing pages event programs, training modules, project plans, technical guides, case studies, and product catalogs.

The server 104 is further configured to operate the interactive PDF as a distribution platform that integrates content, communication, and transactional workflows into a single portable document, enabling use across healthcare, education, distance learning system, publishing system, sales enablement, corporate training, insurance, financial services, government, enterprise workflows and military programs. All data collected from users and exchanged during chat or group messaging sessions is securely transmitted and stored in compliance with applicable healthcare data privacy regulations, including the Health Insurance Portability and Accountability Act (HIPAA).

The server 104 is further configured to enable multi-user interaction within the interactive PDF, including inviting additional users to join live sessions, collaborate in real time, submit data, complete transactions, and participate in communication sessions without leaving the interactive PDF.

The server 104 is further configured to leverage a communication and data-exchange engine to enable zero-installation, frictionless access to interactive PDFs across any web application or device, thereby eliminating the need for portals, custom integrations, or client-side software installations.

The system is configured to embed video, chat, and forms in books and publications, making it suitable for educational purposes and an effective tool for driving sales and promotions in brochures and presentations, thereby transforming the document into a powerful sales engine. The system is configured to secure all content within interactive PDF through encryption. The interactive PDF opens instantly through a simple URL and behaves like a flipping-book application, optimized for both desktop and mobile users.

The system is configured to allow recording of live video on top of the interactive PDF, making it ideal for reviewing test results with a patient or customer. The system creates an entirely new distribution channel for communication, telemedicine, education, publishing, and enterprise workflows.

LivePDFT™ effectively upgrades billions of documents already in circulation and is built on the same communication and data-exchange engine that powers LiveNetworks™, with the major advantage of zero installation, zero friction, and universal compatibility. The system bypasses traditional barriers including app downloads, browser extensions, electronic medical record (EMR) and electronic health record (EHR) integration projects, multi-system training, and security reviews for client-side installs. Inside the interactive PDF, users can ask questions in real time, speak with a provider or instructor, submit forms, view reports, watch embedded videos, make payments, complete transactions, and invite others to join a live session. This 'document as platform' approach collapses entire workflows into one interface. LivePDFT™ converts the world's most widely used document format into an interactive, service-enabled application layer that reduces friction, expands distribution, and enables transactions directly inside content."

FIG. 2 exemplarily illustrates a block diagram 200 of a server 104, according to an embodiment of the present invention. The server 104 comprises a processor 202 and a memory 204 storing a set of instructions executable by the processor 202. The instructions comprising a software module. In one embodiment, the software module comprises the document generation and execution module 206, the instant communication module 208, the link generation module 210, and the link detection and processing module 212. The document generation and execution module 206 is configured to generate an interactive portable document format (PDF) via the user device (102, 108) associated with the user and connected to the server 104. The interactive PDF comprises multimedia content including images, animations, and video streams. The document generation and execution module 206 is further configured to execute or inject the interactive portable document format (PDF) over a web application executed in a browser environment.

The instant communication module 208 is configured to integrate and display one or more interfaces of one or more Enterprise Messaging Network services over the interactive PDF. The instant communication module 208 is configured to enable real-time communication, including video conferencing and messaging, between users via the Enterprise Messaging Network services. A cross-domain configuration framework, implemented on the server 104, enables secure and permissioned interaction of the system with external websites, third-party applications, and social media platforms while maintaining compliance with healthcare data privacy requirements. Upon user interaction with the displayed interface, the system activates HIPAA-compliant, enterprise-grade content messaging and chat, forms, scheduling, and live video conferencing features.

The link generation module 210 is configured to generate a unique uniform resource locator (URL) identifying the generated interactive PDF. The link detection and processing module 212 is configured to detect links and determine whether such links are associated with live network or live network server. In one embodiment, upon detecting the link associated with the live network, the system is configured to execute one or more services on top of the interactive PDF document or the application. The system is configured to execute one or more services on the interactive PDF on top of the application. The services include multimedia content images, animations, video streams and execution of embedded interfaces.

In one embodiment, the system provides an extension or software plugin configured to identify links, including special links within an application environment and to determine whether such links are associated with one or more live network services. Upon identification, the system is able to activate and provide one or more services, including chat, video conferencing, reports, forms, related interactive services or any other embedded services.

The system can seamlessly empower any application, including enterprise applications such as an Oracle® database, by enabling a user to insert a link anywhere on a displayed page. The links or activated links include, but not limited to, text or image links. The inserted link activates the associated live network services. In this manner, the system empowers the application without requiring modification of application code or the addition of a single line of code.

The system further enables insertion of specific links into an existing portable document format (PDF) document or, alternatively, creation of a new PDF from scratch. The inserted links activate the associated live network services when detected and executed by the system.

In one embodiment, the document generation and execution module 206 is configured to generate the interactive portable document format (PDF) from scratch or by enhancing existing PDFs. The document generation and execution module 206 is further configured to provide one or more options to create the interactive portable document format, including a text option configured to add, edit, or remove text within the interactive PDF, an image option configured to add or remove images within the interactive PDF, a shape option configured to add or manipulate graphical shapes within the interactive PDF, and a free-drawing option configured to enable freehand drawing within the interactive PDF. The document generation and execution module 206 further provides a video embedding option configured to embed video content, including third-party video sources, within the interactive PDF, and an audio option configured to embed audio content within the interactive PDF. The document generation and execution module 206 further provides a report option configured to add or generate report content within the interactive PDF, a form option configured to add interactive forms within the interactive PDF, a link option configured to embed selectable hyperlinks within the interactive PDF, and an upload option configured to enable file uploads within the interactive PDF.

In one embodiment, the generated interactive PDF is embedded with one or more embedded interfaces. The embedded interfaces include a communication interface configured to enable real-time chat, audio communication, and video conferencing within the interactive PDF, a payment processing interface configured to enable payment transactions within the interactive PDF, and a scheduling interface configured to enable appointment scheduling within the interactive PDF. The embedded interfaces further include a database lookup interface configured to enable querying and retrieval of data from one or more databases 110 within the interactive PDF, and a media playback interface configured to provide text-to-speech, recorded audio playback, and inline media playback within the interactive PDF. The embedded interfaces further include a chart generation interface configured to dynamically create one or more charts by selecting data provided within the interactive PDF. The chart generation interface is further configured to enable a user to search, filter, and rearrange columns of data provided within the interactive PDF and to dynamically generate one or more charts based on the selected data.

In one embodiment, execution of the live, interactive PDF produces a technical effect by transforming a static document into a real-time, network-connected execution environment for data management, secure communication, multimedia rendering, and structured data exchange.

In one embodiment, the Enterprise Messaging Network services include a live video conferencing service, an instant messaging and notifications service, a group messaging service, and a direct file sharing service. The instant communication module 208 is bi-directional and configured to enable the Enterprise Messaging Network to communicate with other users. The user devices (102, 108), the Enterprise Messaging Network, and the server 104 are in communication via the communication network 106.

In one embodiment, the Enterprise Messaging Network device includes one or more computing devices with computational capability connected to the communication network 106. The user devices (102, 108) are at least one of a tablet computer, personal computer, personal digital assistant, smart phone, smart television, palm-top device, phablet, laptop, or another device with computational capability connected to the communication network 106.

In one embodiment, the server 104 further includes a portal software module executed by the processor 202, wherein the portal software module is configured to provide users with an interface to generate the interactive PDF. In one embodiment, the interactive PDF is accessible through a uniform resource locator (URL) and launches instantly without requiring installation of software applications, browser extensions, or plugin components.

Figure 3:
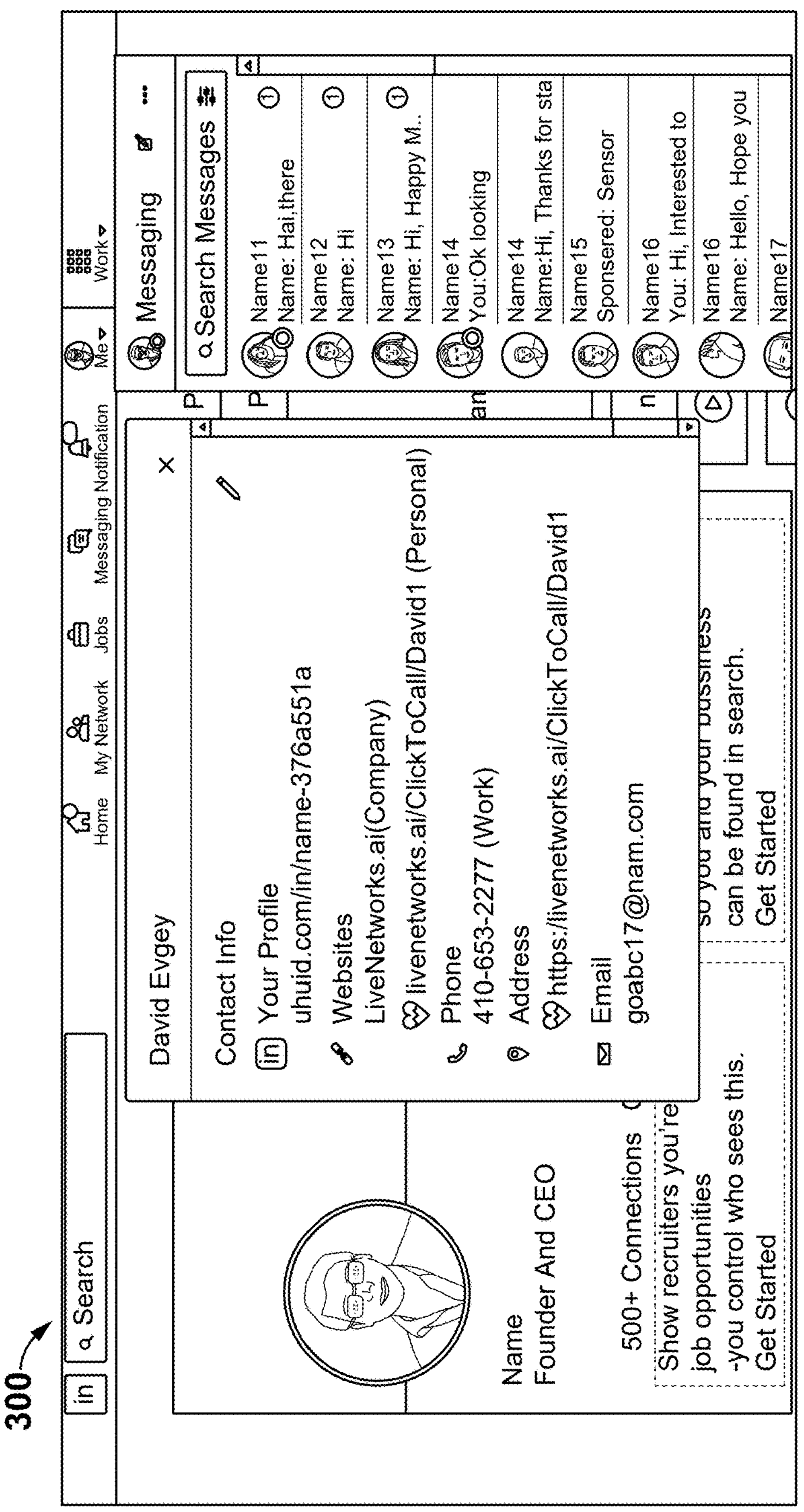
FIG. 3 exemplarily illustrates a screenshot of a user interface displaying a link to an interactive portable document format (PDF) document on a profile displayed within a social media platform, according to one embodiment of the present invention.

FIG. 3 exemplarily illustrates a screenshot 300 of a user interface displaying a link to an interactive portable document format (PDF) document on a profile displayed within a social media platform, according to one embodiment of the present invention.

Figure 4:
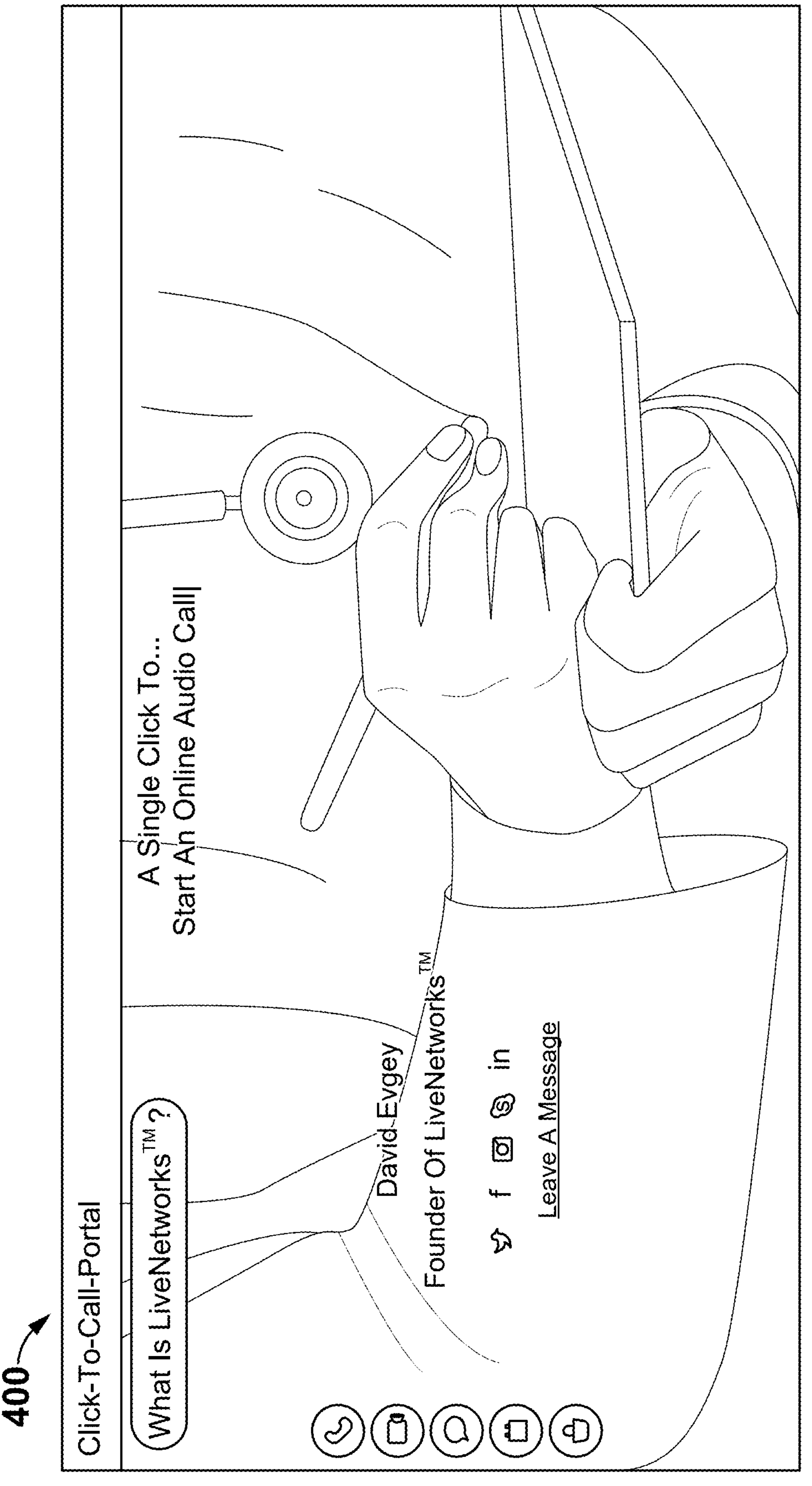
FIG. 4 exemplarily illustrates a screenshot of a user interface of an interactive PDF displaying one or more communication interfaces, according to an embodiment of the present invention.

FIG. 4 exemplarily illustrates a screenshot 400 of a user interface of an interactive PDF displaying one or more communication interfaces, according to an embodiment of the present invention. The interfaces provide one or more functions including least one of, requesting an audio call, requesting a video conference, initiating a chat, scheduling a meeting, and exchange of interactive forms and structured data.

Figure 5:
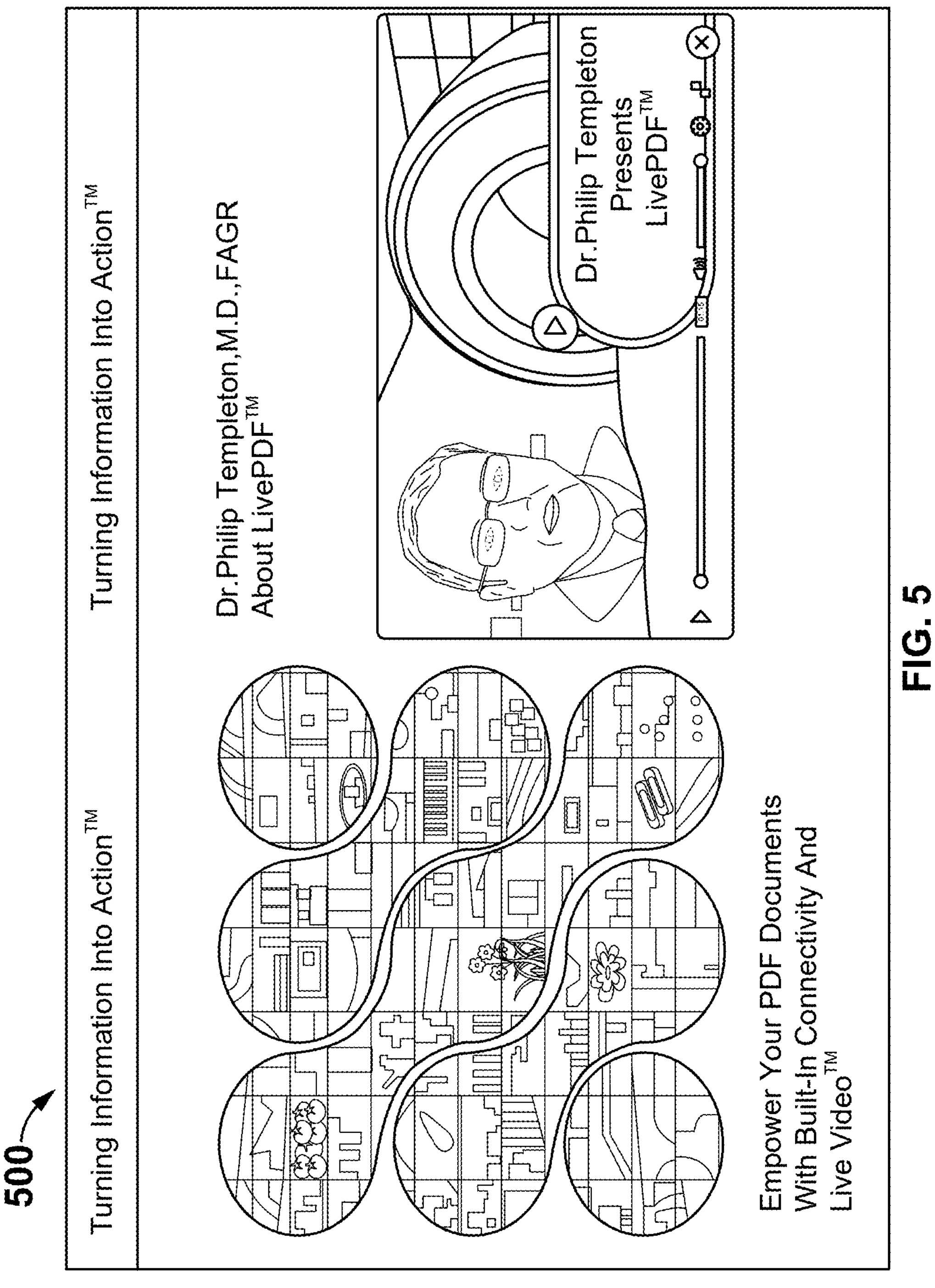
FIG. 5 exemplarily illustrates a screenshot of a user interface of an interactive portable document format (PDF)

FIG. 5 exemplarily illustrates a screenshot 500 of a user interface of an interactive portable document format (PDF) document displaying video content, according to an embodiment of the present invention.

FIG. 6 exemplarily illustrates a screenshot 600 of a user interface comprising one or more options to create the interactive PDF, according to an embodiment of the present invention. The options, include but not limited to, selecting text, image, shape, drawing, video, audio, report, form, click-to-live network, and uploads and links. Further, the user interface provides an option to view the edited contents in PDF format through a "view in PDF" option.

FIG. 7 exemplarily illustrates a screenshot 700 of a user interface to add a video in the interactive PDF, according to an embodiment of the present invention. An image added to the interactive PDF is displayed within the user interface. Video content is added by a user by selecting a video option and providing a uniform resource locator (URL) corresponding to video content hosted on an external website. In one embodiment, the video is added by selecting the video option and supplying a link associated with the video content.

FIG. 8 exemplarily illustrates a screenshot 800 of a user interface to add text with a hyperlink to the interactive PDF, according to an embodiment of the present invention. The user interface provides a text option selectable by the user. Upon selection, textual content is added. The textual content comprises a header, graphical text, a sub-header, and body text. In one embodiment, the user interface enables the user to associate a report with selected text by adding a hyperlink to the text. The activation of the hyperlink displays or opens the associated report within the interactive PDF.

FIG. 9 exemplarily illustrates a screenshot 900 of a user interface displaying the edited interactive PDF, according to an embodiment of the present invention. The interactive PDF displaying an image, a video, and a report.

FIG. 10 exemplarily illustrates a screenshot 1000 of a user interface displaying a report added with the text of FIG. 8 via the hyperlink, according to an embodiment of the present invention. Upon clicking the text with a hyperlink to the report, the report opens over the interactive PDF. The report is displayed in a tabular format, comprising a plurality of data arranged in multiple columns with column headers. The interactive PDF enables the user to perform at least one of the following operations on the report including copy, copy with headers, paste, create a chart, and export.

FIG. 11 exemplarily illustrates a screenshot 1100 of the interactive PDF displaying a pie chart generated from data of the report of FIG. 10 using the options provided within the interactive PDF, according to an embodiment of the present invention. The interactive PDF further provides options to generate different types of charts, edit the report, and update the charts accordingly.

FIG. 12A-12J illustrates, by example, the full range of interactive elements that can be embedded in an interactive PDF (LivePDF) document and demonstrated in real time. LivePDF enables PDFs to be enhanced with rich media and services, including YouTube videos; recorded or streaming video; images; animated GIF and SVG files that run or play automatically within the PDF; chat, live video conferencing and scheduling links that, when selected, open interactive pop-up windows displaying phone, conferencing, or related service options; and audio playback. LivePDF further enables the creation of audio files directly within the LivePDF editor, wherein selecting an audio element plays the corresponding sound with customizable visual effects synchronized to the audio content. Additional capabilities include Excel-based reports, charts, or tables generated by capturing or selecting data from any web page; single- or multi-page forms; and the execution of mini-applications or services within pop-up windows.

Advantageously, the system offers a dynamic, monetizable platform through the interactive PDF, making it applicable across diverse areas of use. The system utilizes the interactive PDF in domains including health systems and payers, education and distance learning, publishers, corporate training, sales enablement, customer onboarding, insurance and financial services, and government and military programs. The system delivers entire workflows inside the interactive PDF without requiring external portals, applications, or custom integrations.

The system enables a user to invite other users to join a call or live session. In one example, a service provider sells interactive books, courses, and professional content through the interactive PDF. The system authenticates any consumer over the live network for content viewing. In another example, health systems, employers, and government agencies use the interactive PDF for telemedicine, health data capture and reporting, patient or member education, workflow automation, staff training, and high-compliance communication.

The interactive PDF embeds micro-applications within the document. The micro-applications include, without limitation, payment, calculator, scheduling, and search utilities. The interactive PDF functions as a distribution platform that merges content, communication, and transactions into a single portable container. The interactive PDF runs inside any electronic medical record (EMR), any web application, and any device without requiring integration work, thereby reducing adoption friction and implementation costs. The interactive PDF further finds application in landing pages, music albums, and similar digital content delivery formats.

The system enables the user accessing the interactive PDF to ask queries to a service provider in real time, speak with the service provider, submit forms, view reports, watch embedded videos, make payments, complete transactions, and invite others to join a live session, all without leaving the interactive PDF.

In one embodiment, the system further comprises an editor configured to facilitate authoring, insertion, and orchestration of interactive elements within a LivePDF document. The editor operates solely as a composition and configuration interface and does not alter the execution environment, runtime behavior, or communication architecture of the LivePDF system disclosed in the parent application. In one embodiment, the interactive PDF further supports animated image formats including GIF and SVG images that automatically render and animate inline within the document upon execution. In one embodiment, the interactive PDF supports spreadsheet-like structured data tables derived from external applications or uploaded spreadsheet files, including Excel-compatible formats, without requiring Microsoft Office or third-party spreadsheet software. The tables support searching, sorting, filtering, column rearrangement, selection of rectangular data ranges, and dynamic generation of charts based on the selected data. In one embodiment, the interactive PDF supports embedded audio playback including MP3 audio files that play directly within the document interface without launching external media players.

In one embodiment, the interactive PDF embeds executable micro-tools that function as lightweight, task-specific applications activated by selectable links within the document. The micro-tools execute within the LivePDF environment and provide services including database search, calculation, lookup, scheduling, or transactional operations. In one example, a document related to diabetes enables execution of a nutrition database micro-tool that searches hundreds of thousands of food records to retrieve sugar content, vitamin data, and mineral information. In one embodiment, the interactive PDF supports document chaining, wherein activation of a link within a first LivePDF document launches a second LivePDF document, enabling construction of multi-document books, lesson plans, training courses, or modular content systems while preserving full interactivity within each document.

Although a single embodiment of the invention has been illustrated in the accompanying drawings and described in the above detailed description, it will be understood that the invention is not limited to the embodiment developed herein, but is capable of numerous rearrangements, modifications, substitutions of parts and elements without departing from the spirit and scope of the invention.

The foregoing description comprises illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

The invention claimed is:

1. A system, comprising:

a server;

a processor; and a memory storing instructions executed by the processor, the instructions comprising a software module, wherein the software module communicates directly with a LiveNetworks server and further comprises:

a document generation and execution module configured to:

generate an interactive portable document format (PDF) via a user device associated with the user and connected to the server, wherein the interactive PDF comprises multimedia content images, animations, and video streams, and execute or inject the interactive portable document format (PDF) over a web application executed in a;

an instant communication module configured to:

integrate and display one or more interfaces of one or more Enterprise Messaging Network services over the interactive PDF;

enable real-time communication, including video conferencing and messaging, between the users via said Enterprise Messaging Network services, and a cross-domain configuration framework, implemented on the server, enabling secure, permissioned interaction of the software module with external websites, third-party applications, and social media platforms while maintaining compliance with healthcare data privacy requirements, and upon user clicking on the one or more interfaces, the system activates Health Insurance Portability and Accountability Act (HIPAA) compliant, enterprise-grade content messaging and chat, forms, scheduling and live video conferencing features, a link generation module configured to:

generate a unique uniform resource locator (URL) identifying the generated interactive PDF, wherein the interactive PDF is accessible through the uniform resource locator (URL) and launches instantly without requiring installation of software applications, browser extensions, or plugin components, and a link detection and processing module configured to:

detect links and determine whether such links are associated with the LiveNetworks server, and upon detecting the link associated with the LiveNetworks server, the system is configured to execute one or more services on top of the web application, execute one or more services on top of the interactive PDF document or execute the interactive PDF on top of the web application based on the detected link, wherein the services include multimedia content images, animations, video streams and execution of embedded interfaces, wherein the execution of the interactive PDF produces a technical effect by transforming a static document into a real-time, network-connected execution environment for data management, secure communication, multimedia rendering and structured data exchange.

2. The system of claim 1, wherein the document generation and execution module is configured to:

generate the interactive portable document format (PDF) from scratch or by enhancing existing PDFs, and provide one or more options to create the interactive portable document format, wherein the options include:

a text option configured to add, edit, or remove text within the interactive PDF;

an image option configured to add or remove images within the interactive PDF;

a shape option configured to add or manipulate graphical shapes within the interactive PDF;

a free-drawing option configured to enable freehand drawing within the interactive PDF;

a video embedding option configured to embed video content, including recorded or streaming video sources residing in remote servers belonging to LiveNetworks or other third-parties, within the interactive PDF;

an audio option configured to embed audio content within the interactive PDF;

a report option configured to add or generate report content within the interactive PDF;

a form option configured to add interactive forms within the interactive PDF;

a link option configured to embed selectable hyperlinks within the interactive PDF, and an upload option configured to enable file uploads within the interactive PDF.

3. The system of claim 1, wherein the generated interactive PDF is embedded with one or more embedded interfaces, wherein the one or more embedded interface comprises:

a communication interface configured to enable real-time chat, audio communication, and video conferencing within the interactive PDF;

a payment processing interface configured to enable payment transactions within the interactive PDF;

a scheduling interface configured to enable appointment scheduling within the interactive PDF;

a database lookup interface configured to enable querying and retrieval of data from one or more databases within the interactive PDF;

a media playback interface configured to provide text-to-speech, recorded audio playback, and inline media playback within the interactive PDF, and a chart generation interface configured to dynamically create one or more charts by selecting data provided within the interactive PDF, wherein the chart generation interface is configured to enable the user to search, filter, and rearrange columns of data provided within the interactive PDF, and to dynamically generate one or more charts based on the selected data.

4. The system of claim 3, wherein the chart generation interface dynamically generates charts based on a user-selected region of data within a structured data table displayed inside the interactive PDF.

5. The system of claim 1, wherein the one or more Enterprise Messaging Network services includes a live video conferencing service, an instant messaging service and notifications service, a group messaging service and a file sharing service.

6. The system of claim 1, wherein the instant communication module is bi-directional and configured to enable an Enterprise Messaging Network to communicate with other users.

7. The system of claim 1, wherein the user devices, the Enterprise Messaging Network, and the server are in communication via a communication network.

8. The system of claim 1, wherein the user devices are at least one of a tablet computer, personnel computer, personnel digital assistant, smart phone, smart television, palm top, phablet, laptop, or a device with computational capability connected to the communication network.

9. The system of claim 1, wherein the server further includes a portal software module executed by the processor, wherein the portal software module is configured to provide users an interface to generate the interactive pdf.

10. The system of claim 1, wherein the interactive PDF supports animated image formats including GIF and SVG images that automatically render and animate inline within the document.

11. The system of claim 1, enables users to install a browser extension and monitor new incoming messages, presence of visitors in online meeting rooms for video conferencing, capturing visible data on screen as screen shots, record a video of applications work, capture data in tables, and securely share the information with an individual or a group using a push of a button.

12. The system of claim 1, wherein the interactive PDF supports embedded audio playback including MP3 audio files that play directly within the one or more interfaces.

13. The system of claim 1, wherein the interactive PDF embeds one or more micro-tools activated by selectable links, the micro-tools executing within the interactive PDF to provide task-specific services including database search, lookup, calculation, or transactional operations.

14. The system of claim 1, wherein activation of a link within a first interactive PDF launches a second interactive PDF, enabling chained execution of multiple interactive PDF documents within a unified workflow.

15. The system of claim 1, enables the user to insert the link anywhere on a displayed interface or application and the system enables the inserted link to activate the associated services of live network server, thereby seamlessly empowering any application, wherein the links or activated links include, but not limited to, text or image links.

16. The system of claim 1, enables the user to manage permissions and to determine who get access to the document by indicating a registered user name, member(s) of a chat group so only specific users login with user name and password or only registered users subscribed and members of the chat group can access the document, wherein the permissions can determine also if access is viewing only or editing the document, or only registered users who paid for the document such a book or a course, thereby this method is an easy yet secure and effective, to manage permissions.

17. The system of claim 1, wherein the interactive PDF supports spreadsheet-like structured data tables derived from uploaded spreadsheet files without requiring third-party spreadsheet software, or by capturing structured data in tables from the web using a browser extension provided by Livenetworks as described claim 11 hereafter, the tables enabling searching, sorting, filtering, selection of data ranges, and dynamic chart generation.

* * * * *